US010793540B2

(12) United States Patent
Kashiwaba et al.

(10) Patent No.: US 10,793,540 B2
(45) Date of Patent: *Oct. 6, 2020

(54) METHOD FOR PRODUCING FLUORINE-CONTAINING CYCLOPROPANE CARBOXYLIC ACID COMPOUND

(71) Applicant: Central Glass Company, Limited, Ube-shi, Yamaguchi (JP)

(72) Inventors: Takashi Kashiwaba, Kawagoe (JP); Takako Yamazaki, Kawagoe (JP); Shoko Ishii, Kawagoe (JP); Shunsuke Mimura, Kawagoe (JP); Masanori Fushimi, Ube (JP); Ryuichi Okamoto, Kawagoe (JP); Haruki Kobayashi, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/562,214

(22) Filed: Sep. 5, 2019

(65) Prior Publication Data

US 2019/0389831 A1 Dec. 26, 2019

Related U.S. Application Data

(63) Continuation of application No. 15/741,020, filed as application No. PCT/JP2016/068748 on Jun. 24, 2016.

(30) Foreign Application Priority Data

Jun. 29, 2015 (JP) ................................. 2015-129628

(51) Int. Cl.
| | |
|---|---|
| *C07D 327/10* | (2006.01) |
| *C07C 67/343* | (2006.01) |
| *C07C 67/52* | (2006.01) |
| *C07C 69/74* | (2006.01) |
| *C07C 67/313* | (2006.01) |
| *C07C 67/08* | (2006.01) |
| *C07C 211/27* | (2006.01) |
| *C07B 57/00* | (2006.01) |

(52) U.S. Cl.
CPC ............ *C07D 327/10* (2013.01); *C07C 67/08* (2013.01); *C07C 67/313* (2013.01); *C07C 67/343* (2013.01); *C07C 67/52* (2013.01); *C07C 69/74* (2013.01); *C07C 211/27* (2013.01); *C07B 57/00* (2013.01); *C07C 2601/02* (2017.05)

(58) Field of Classification Search
CPC .................................................... C07D 327/10
USPC ........................................................ 549/34
See application file for complete search history.

(56) References Cited

U.S. PATENT DOCUMENTS

| 10,450,291 | B2 * | 10/2019 | Kashiwaba .......... C07D 327/10 |
| 2009/0274657 | A1 | 11/2009 | Gai et al. |
| 2011/0201825 | A1 | 8/2011 | Ishii et al. |
| 2011/0213176 | A1 | 9/2011 | Ishii et al. |
| 2011/0245529 | A1 | 10/2011 | Tanaka et al. |
| 2015/0175626 | A1 | 6/2015 | Cagulada et al. |
| 2015/0284368 | A1 | 10/2015 | Kuduk et al. |

FOREIGN PATENT DOCUMENTS

| JP | 2006-328011 A | 12/2006 |
| JP | 2008-230970 A | 10/2008 |
| WO | WO 2009/134987 A1 | 11/2009 |
| WO | WO 2010/041739 A1 | 4/2010 |
| WO | WO 2014/078220 A1 | 5/2014 |

OTHER PUBLICATIONS

Tang, Org. Process Res. Dev. 2011, 15, 1207-1211.*
Rancourt J. et al., "Peptide-Based Inhibitors of the Hepatitis C Virus NS3 Protease : Structure-Activity Relationship at the C-Terminal Position", J. Med. Chem., 2004, vol. 47, pp. 2511-2522.
Kasai N. et al. "A Practical Synthesis and Applications of (E)-Diphenyl-β-(trifluoromethyl)vinylsulfonium Triflate," Synthesis, 2012, vol. 44, pp. 3489-3495.
Jiang B. et al, "A Convenient Stereoselective Synthesis of Trifluoromethyl-substituted Polyfunctionalized Cyclopropane: Synthesis of Trans-trifluoronorcoronamic Acid," Chem. Commun., 2003, pp. 536-537.
Gao Y. et al., "Vicinal Diol Cyclic Sulfates: Like Epoxides Only More Reactive," J. Am. Chem. Soc., 1988, vol. 110, pp. 7538-7539.
Tang W. et al., "A Practical Asymmetric Synthesis of Isopropyl (1R, 2S)-Dehydrocoronamate," Organic Process Research & Development., 2011, vol. 15, pp. 1207-1211.

(Continued)

*Primary Examiner* — Nizal S Chandrakumar
(74) *Attorney, Agent, or Firm* — Crowell & Moring LLP

(57) ABSTRACT

The present invention provides an industrially applicable method for production of a fluorine-containing cyclopropane carboxylic acid compound useful as an intermediate for pharmaceutical and agrichemical products. A fluorine-containing cyclopropane monoester is obtained by: forming a fluorine-containing cyclic sulfate with the use of a fluorine-containing diol compound and sulfuryl fluoride (as a cyclic sulfuric esterification step); reacting the fluorine-containing cyclic sulfate with a malonic diester, thereby forming a fluorine-containing cyclopropane diester (as a cyclopropanation step); and hydrolyzing the fluorine-containing cyclopropane diester (as a hydrolysis step). The fluorine-containing cyclopropane carboxylic acid compound, such as fluorine-containing cyclopropane monoester or its salt, can be obtained with high chemical and optical purity by mixing the fluorine-containing cyclopropane monoester with an amine and subjecting the resulting salt of the fluorine-containing cyclopropane monoester and amine to recrystallization purification.

12 Claims, No Drawings

(56) References Cited

OTHER PUBLICATIONS

International Search Report (PCT/ISA/210) issued in PCT Application No. PCT/JP2016/068748 dated Sep. 6, 2016 with English-language translation (Five (5) pages).
Japanese-language Written Opinion (PCT/ISA/237) issued in PCT/JP2016/068748 dated Sep. 6, 2016 (Six (6) pages).
Karadeolian A. et al., "Examination of Homo-[3+2]-Dipolar Cycloaddition: Mechanistic Insight into Regio- and Diastereoselectivity," The Journal of Organic Chemistry, 2007, vol. 72, No. 26, pp. 10251-10253.
Burgess K. et al., "Synthesis of a Valuable Cyclopropyl Chiron for Preparations of 2,3-Methanoamino Acids," The Journal of Organic Chemistry, 1993, vol. 58, No. 14, pp. 3767-3768.
Jiang, Chemical Communications (Cambridge, United Kingdom) (2003), (4), 536-537.
Hercouet, Tetrahedron: Asymmetry, 9(13), 2233-2234; 1998.

\* cited by examiner

METHOD FOR PRODUCING FLUORINE-CONTAINING CYCLOPROPANE CARBOXYLIC ACID COMPOUND

CROSS REFERENCE TO RELATED APPLICATIONS

This application is a continuation of U.S. application Ser. No. 15/741,020, filed Dec. 29, 2017, which is a 371 of International Application No., PCT/JP2016/068748 filed Jun. 24, 2016, which claims priority from Japanese Patent Application No. 2015-129628, filed Jun. 29, 2015, the disclosures of which are expressly incorporated by reference herein.

FIELD OF THE INVENTION

The present invention relates to a method for producing a fluorine-containing cyclopropane carboxylic acid compound.

BACKGROUND ART

As a peripheral technology of fluorine-containing cyclopropane carboxylic acid compounds, Non-Patent Document 1 reports a method of producing a fluorine-free cyclopropane diester with the use of a compound having two leaving groups in the molecule as a raw material (see the following scheme).

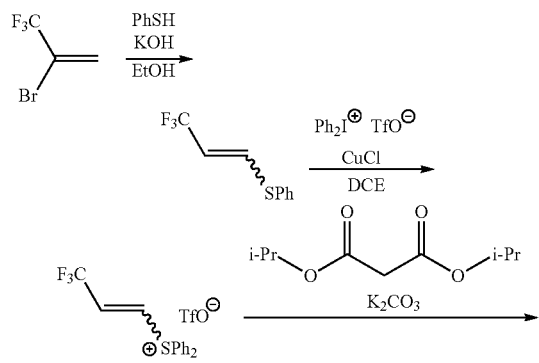

Non-Patent Document 2 reports a method of producing a fluorine-containing cyclopropane diester via a sulfonium salt (see the following scheme).

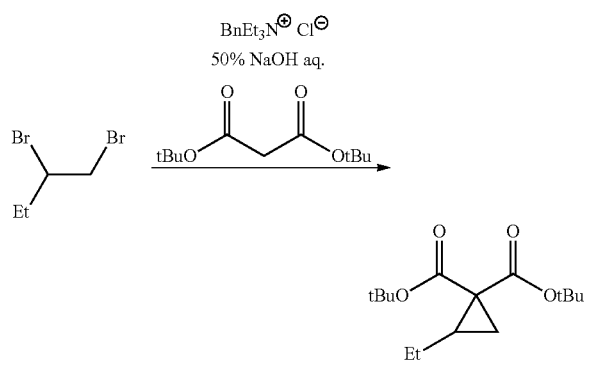

-continued

Further, Non-Patent Document 3 reports a method of synthesizing a fluorine-containing cyclopropane monoester with the use of bromotrifluoropropene.

Patent Document 1 reports a method of producing a salt with the use of difluoroacetaldehyde ethyl hemiacetal (see the following scheme).

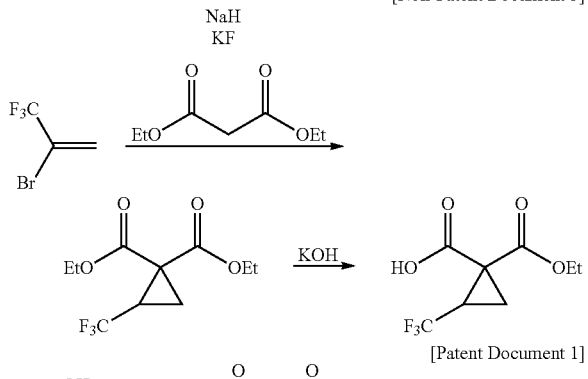

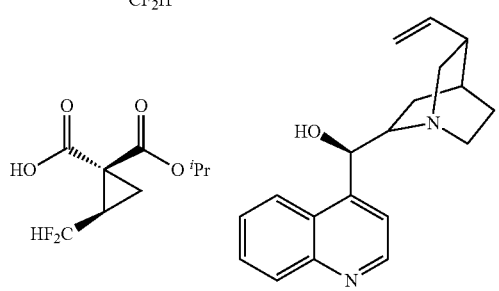

As a technique for production of a cyclopropane diester, Non-Patent Document 4 reports a method of synthesizing a cyclic sulfate and a malonic diester (see the following scheme).

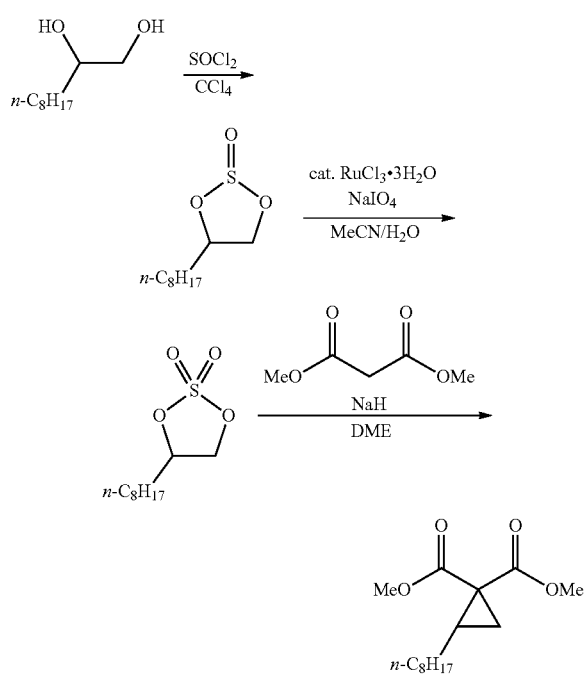

There have however been reported no production examples of a fluorine-containing cyclopropane diester represented by the following formula and a fluorine-containing cyclopropane monoester represented by the following formula.

On the other hand, as a conventional technique relevant to synthesis of a fluorine-containing cyclic sulfate as a starting raw material for production of fluorine-containing cyclopropane carboxylic acid compounds, Patent Document 2 discloses a method of forming a fluorine-containing cyclic sulfate by reacting 1,1,1-trifluoro-2,3-propanediol with sulfuryl fluoride in the presence of imidazole (see the following scheme).

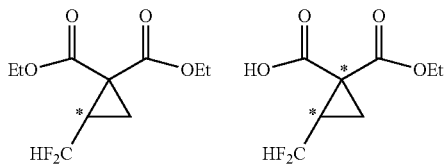

Patent Document 3 discloses a method of forming a fluorine-containing cyclic sulfate with the use of a diol compound, triethylamine and sulfuryl chloride (see the following scheme).

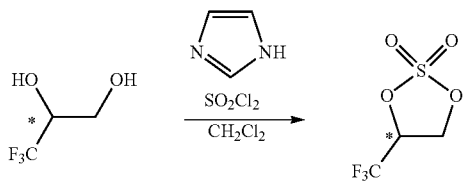

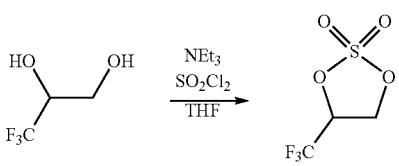

However, there has been reported no production example of a fluorine-containing cyclic sulfate represented by the following formula.

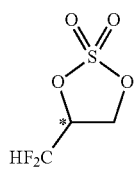

PRIOR ART DOCUMENTS

Patent Documents

Patent Document 1: U.S. Patent Publication No. 2015/0175626
Patent Document 2: Japanese Laid-Open Patent Publication No. 2006-328011
Patent Document 3: Japanese Laid-Open Patent Publication No. 2008-230970

Non-Patent Documents

Non-Patent Document 1: J. Med. Chem., 2004, vol. 47, p. 2511-2522
Non-Patent Document 2: Synthesis, 2012, vol. 44, p. 3489-3495
Non-Patent Document 3: Chem. Commun., 2003, p. 536-537
Non-Patent Document 4: J. Am. Chem. Soc., 1988, vol. 110, p. 7538-7539

SUMMARY OF THE INVENTION

Problems to be Solved by the Invention

It is an object of the present invention to provide a method for industrial production of a fluorine-containing cyclopropane carboxylic acid compound.

By reference to the production method of the cyclopropane diester as disclosed in Non-Patent Document 1, researches have been made to produce a fluorine-containing cyclopropane dicarboxylic acid compound with the use of a compound having two leaving groups in the molecule. However, the target compound cannot be obtained by such researches (see the after-mentioned Comparative Examples 4, 6 and 8).

The method disclosed in Non-Patent Document 2 is high in yield and seems to be favorable. It is however difficult to industrially apply this method because of the need to use an expensive iodonium salt.

The method disclosed in Non-Patent Document 3 is also high in yield and seems to be favorable. In this method, however, the fluorine-containing cyclopropane monoester is obtained as a racemic mixture. In the case where the target compound is an optically active isomer, the yield of the target optical isomer becomes half or less by optical resolution. It is thus somewhat difficult to industrially apply this method.

The method disclosed in Non-Patent Document 4, by which the cyclic sulfate and the malonic diester are synthesized, seems to be favorable. In this method, however, the synthesis of the cyclic sulfate proceeds in two steps and needs to use an expensive transition metal catalyst and highly toxic carbon tetrachloride. It is thus difficult to industrially apply this method.

As mentioned above, the conventional production methods of fluorine-containing cyclopropane carboxylic acid compounds are not satisfactory for industrial applications. Accordingly, the present invention aims to provide an industrially applicable method for production of a fluorine-containing cyclopropane carboxylic acid compound, which is important as an intermediate for pharmaceutical and agrichemical products.

Means for Solving the Problems

As a result of extensive researches made in view of the above-mentioned conventional problems, the present inventors have found a production process indicated in the following scheme and then accomplished an industrially applicable production method of a fluorine-containing cyclopropane monoester salt. More specifically, it has been found that, as compared to the conventional production methods, it is possible to produce a fluorine-containing cyclopropane monoester under industrially easily applicable conditions through the following steps: a "cyclic sulfuric esterification step" of forming a fluorine-containing cyclic sulfate by reaction of a fluorine-containing diol compound with sulfuryl fluoride; a "cyclopropanation step" of forming a fluorine-containing cyclopropane diester by reacting the fluorine-containing cyclic sulfate obtained in the preceding step with a malonic diester; and a "hydrolysis step" of hydrolyzing the fluorine-containing cyclopropane diester obtained in the preceding step. It has also been found that it is possible to obtain a fluorine-containing cyclopropane carboxylic acid compound such as fluorine-containing cyclopropane monoester salt with high chemical and optical purity by a "recrystallization step" of mixing the fluorine-containing cyclopropane monoester obtained in the preceding step with an amine, thereby forming a salt of the fluorine-containing cyclopropane monoester and the amine, and then, purifying the salt by recrystallization.

The present invention has been accomplished based on these findings.

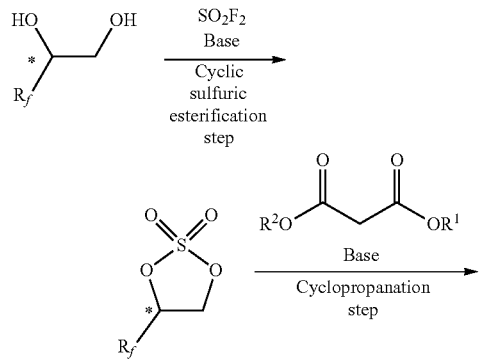

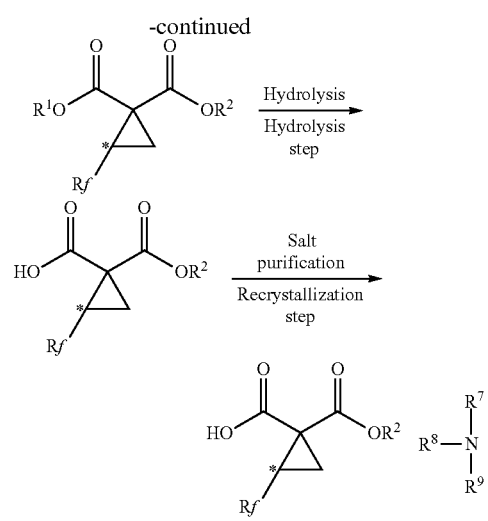

There are expected some problems in comparison of the production steps of the present invention with Patent Documents 2 and 3.

The method disclosed in Patent Document 2 seems to be favorable because it is possible to obtain the fluorine-containing cyclic sulfate with high yield. However, this method needs to use highly toxic methylene chloride. In addition, it is not possible to obtain the target compound by this method in the case of replacing a trifluoromethyl group of the substrate compound with a partially fluorinated difluoromethyl group, i.e., using the target substrate compound of the present invention (see the after-mentioned Comparative Example 1).

The method disclosed in Patent Document 3 also seems to be favorable because it is possible to obtain the fluorine-containing cyclic sulfate with high yield. It is however not possible to obtain the target compound by this method in the case of replacing a trifluoromethyl group of the substrate compound with a difluoromethyl group (see the after-mentioned Comparative Example 10).

On the other hand, the target substrate compound of the present invention is a fluorine-containing cyclopropane carboxylic acid compound having a high optical purity.

It is conceivable to produce a fluorine-containing cyclopropane carboxylic acid compound by forming a racemic mixture of the fluorine-containing cyclopropane carboxylic acid compound and performing optical resolution of the racemic mixture. In the case where such a method is practically applied, however, the optical resolution of the racemic mixture by recrystallization is inefficient and causes a decrease in yield. In the present invention, by contrast, the optically active compound is used as the raw material so that it is possible to eliminate the step of optical resolution and enable efficient production of the target compound.

The production method of the fluorine-containing cyclopropane carboxylic acid compound according to the present invention is able to solve the problems in the production steps and is industrially highly advantageous.

Namely, the present invention provides a method for producing a fluorine-containing cyclopropane carboxylic acid compound as defined in the following inventive aspects 1 to 16.

[Inventive Aspect 1]

A method of producing a fluorine-containing cyclic sulfate of the general formula [2], comprising: reacting a fluorine-containing diol compound of the general formula

[1] with sulfuryl fluoride in the presence of at least one basic compound selected from the group consisting of alkali metal hydrides, alkaline earth metal hydrides, alkali metal hydroxides, alkaline earth metal hydroxides, alkali metal carbonates, alkaline earth metal carbonates, alkali metal hydrogencarbonates and alkaline earth metal hydrogencarbonates

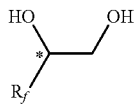

where $R_f$ represents a $C_1$-$C_6$ linear or branched fluoroalkyl group having at least one fluorine atom; and * represents an asymmetric carbon atom

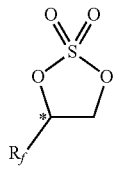

where $R_f$ represents the same group as defined in the general formula [1]; and * represents an asymmetric carbon atom.

[Inventive Aspect 2]

The method according to Inventive Aspect 1, wherein $R_f$ is a difluoromethyl group ($CF_2H$) or a trifluoromethyl group ($CF_3$).

[Inventive Aspect 3]

The method according to Inventive Aspect 1 or 2, wherein the fluorine-containing diol compound is reacted with the sulfuryl fluoride in a temperature range of −50 to +50° C.

[Inventive Aspect 4]

The method according to any one of Inventive Aspects 1 to 3, wherein the sulfuryl fluoride is used in an amount of 0.7 to 4.0 equivalents.

[Inventive Aspect 5]

A method of producing a fluorine-containing cyclopropane diester of the general formula [5] comprising: producing the fluorine-containing cyclic sulfate by the method according to any one of Inventive Aspects 1 to 4; and reacting the fluorine-containing cyclic sulfate with a malonic diester of the general formula [3] in the presence of an inorganic base

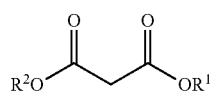

where $R^1$ and $R^2$ each independently represents a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group

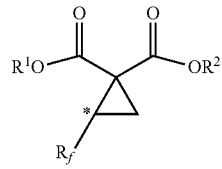

where $R_f$ represents the same group as defined in the general formula [1] of Inventive Aspect 1; $R^1$ and $R^2$ represents the same groups as defined in the general formula [3]; and * represents an asymmetric carbon atom.

[Inventive Aspect 6]

The method according to Inventive Aspect 5, wherein the inorganic base is an alkali metal, an alkali metal hydride, an alkaline earth metal hydride, an alkali metal hydroxide or an alkaline earth metal hydroxide.

[Inventive Aspect 7]

The method according to Inventive Aspect 5 or 6, wherein the fluorine-containing cyclic sulfate of the general formula [2] and the malonic diester of the general formula [3] are added into a solvent containing the inorganic base.

[Inventive Aspect 8]

A method of producing a fluorine-containing cyclopropane monoester of the general formula [7], comprising: producing the fluorine-containing cyclopropane diester by the method according to any one of Inventive Aspects 5 to 7; and performing hydrolysis of the fluorine-containing cyclopropane diester in the presence of an alkali metal hydroxide, alkaline earth metal hydroxide, an alkali metal carbonate, an alkaline earth metal carbonate, an alkali metal hydrogencarbonate, an alkaline earth metal hydrogencarbonate or a quaternary ammonium hydroxide of the general formula [6]

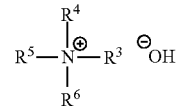

where $R^3$, $R^4$, $R^5$ and $R^6$ each independently represents a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group; and two or more of $R^3$, $R^4$, $R^5$ and $R^6$ may form a part of the same aliphatic ring or aliphatic aromatic ring

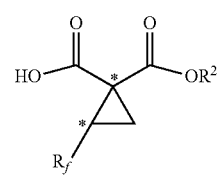

where $R_f$ represents the same group as defined in the general formula [1] of Inventive Aspect 1; $R^2$ represents the same group as defined in the general formula [3] of Inventive Aspect 5; and * represents an asymmetric carbon atom.

[Inventive Aspect 9]

The method according to Inventive Aspect 8, wherein the hydrolysis is performed at a temperature of −30 to +40° C.

[Inventive Aspect 10]

The method according to Inventive Aspect 8 or 9, further comprising: adding an amine of the general formula [8] to the fluorine-containing cyclopropane monoester of the general formula [7], thereby forming a salt of the fluorine-containing cyclopropane monoester and the amine as represented by the general formula [9]; and purifying the salt by recrystallization

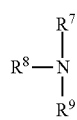

[8]

where $R^7$, $R^8$ and $R^9$ each independently represent a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group

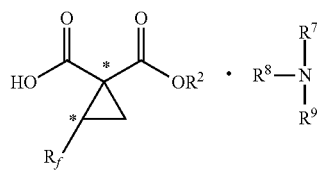

[9]

where $R_f$ represents the same group as defined in the general formula [1]; $R^2$ represents the same group as defined in the general formula [3] of Inventive Aspect 5; and $R^7$, $R^8$ and $R^9$ represent the same groups as defined in the general formula [8].

[Inventive Aspect 11]

The method according to Inventive Aspect 10, wherein the amine of the general formula [8] is an amine of the general formula [10].

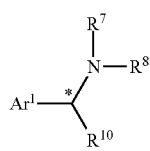

[10]

where $R^7$, $R^8$ and $R^{10}$ each independently represent a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group; $Ar^1$ represents a $C_6$-$C_{14}$ aromatic ring group or substituted aromatic ring group; and, when $R^{10}$ is a $C_1$-$C_{18}$ alkyl group or substituted alkyl group having a linear or branched structure or a cyclic structure (in the case of three or more carbon atoms) or a $C_6$-$C_{18}$ aromatic ring group or substituted aromatic ring group, * represents an asymmetric carbon atom.

[Inventive Aspect 12]

A method of producing a salt of fluorine-containing cyclopropane monoester and 1-phenylethylamine as represented by the general formula [11],

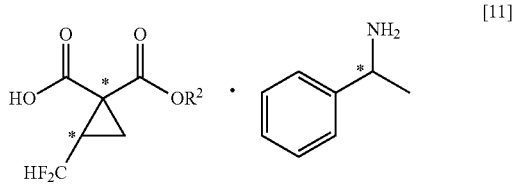

[11]

where $R^2$ represents the same group as defined in the general formula [3] of Inventive Aspect 5; and * represents an asymmetric carbon atom, the method comprising the following steps:

[cyclic sulfuric esterification step] reacting a fluorine-containing diol compound of the formula [12] with an alkali metal hydride, an alkali metal carbonate or an alkali metal hydrogencabonate, and sulfuryl fluoride, thereby forming a fluorine-containing cyclic sulfate of the formula [13],

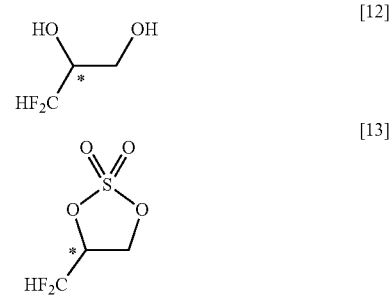

[12]

[13]

where * represents an asymmetric carbon atom

[cyclopropanation step] reacting the fluorine-containing cyclic sulfate obtained in the cyclic sulfuric esterification step with a malonic diester of the general formula [3] in the presence of an alkali metal or an alkali metal hydride, thereby forming a fluorine-containing cyclopropane diester of the general formula [15]

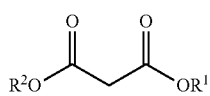

[3]

where $R^1$ and $R^2$ each independently represent a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group

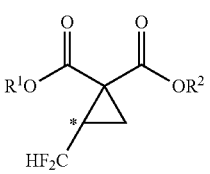

[15]

where $R^1$ and $R^2$ represents the same groups as defined in the general formula [3] of Inventive Aspect 5; and * represents an asymmetric carbon atom

[hydrolysis step] hydrolyzing the fluorine-containing cyclopropane diester obtained in the cyclopropanation step in the presence of an alkali metal hydroxide, an alkali metal carbonate or a quaternary ammonium hydroxide of the general formula [6], thereby forming a fluorine-containing cyclopropane monoester of the general formula [16]

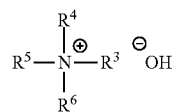

[6]

where $R^3$, $R^4$, $R^5$ and $R^6$ each independently represent a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group; and two or more of $R^3$, $R^4$, $R^5$ and $R^6$ may form a part of the same aliphatic ring or aliphatic aromatic ring

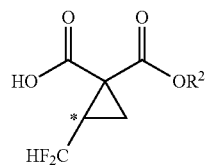

[16]

where $R^2$ represents the same group as defined in the general formula [3] of Inventive Aspect 5; and * represents an asymmetric carbon atom; and

[recrystallization step] adding optically active 1-phenylethylamine to the fluorine-containing cyclopropane monoester formed in the hydrolysis step, thereby forming a salt of the fluorine-containing cyclopropane monoester and 1-phenylethylamine as represented by the formula [11], and then, purifying the salt by recrystallization

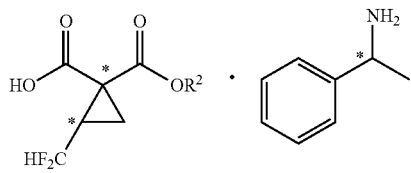

[11]

where $R^2$ represents the same group as defined in the general formula [3].

[Inventive Aspect 13]
A fluorine-containing cyclic sulfate of the formula [13]

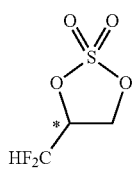

[13]

where * represents an asymmetric carbon atom.

[Inventive Aspect 14]
A salt of fluorine-containing cyclopropane monoester and amine as represented by the formula [17]

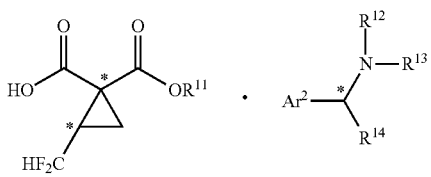

[17]

where $R^{11}$ represents a $C_1$-$C_6$ linear or branched alkyl group; $R^{12}$, $R^{13}$ and $R^{14}$ each independently represent a hydrogen atom, or a $C_1$-$C_6$ linear or branched alkyl group; $Ar^2$ represents a $C_6$-$C_{10}$ aromatic ring group or substituted aromatic ring group; and, when $R^{14}$ is a $C_1$-$C_6$ linear or branched alkyl group, * represents an asymmetric carbon atom.

[Inventive Aspect 15]
A salt of fluorine-containing cyclopropane monoester and 1-phenylethylamine as represented by the formula [18]

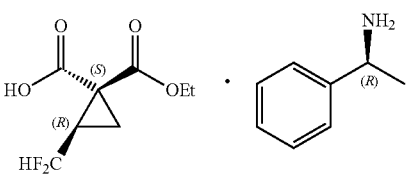

[18]

where Et represents an ethyl group.

[Inventive Aspect 16]
A salt of fluorine-containing cyclopropane monoester and 1-phenylethylamine as represented by the formula [19]

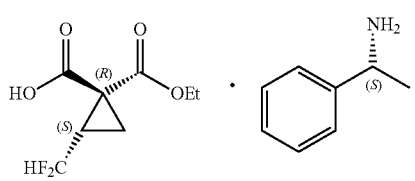

[19]

where Et represents an ethyl group.

It is possible according to the present invention to produce the fluorine-containing cyclopropane carboxylic acid compound such as fluorine-containing cyclopropane monoester salt by the industrially applicable method.

DETAILED DESCRIPTION OF EMBODIMENTS

Hereinafter, the present invention will be described below in detail. It should be understood that: the present invention is not limited to the following embodiments; and various changes and modifications of the following embodiments can be made as appropriate, based on the general knowledge of those skilled in the art, within the range that does not impair the effects of the present invention.

The present invention discloses a method for production of a fluorine-containing cyclopropane carboxylic acid compound and, more specifically, a method of producing a fluorine-containing cyclic sulfate of the general formula [2]

with the use of a fluorine-containing diol compound of the general formula [1] and sulfuryl fluoride (as a cyclic sulfuric esterification step), a method of producing a fluorine-containing cyclopropane diester of the general formula [5] by reacting the fluorine-containing cyclic sulfate obtained by the aforementioned method with a malonic diester (as a cyclopropanation step) and a method of producing a fluorine-containing cyclopropane monoester of the general formula [7] by hydrolyzing the fluorine-containing cyclopropane diester obtained by the aforementioned method (as a hydrolysis step).

It is feasible to convert the fluorine-containing cyclopropane monoester obtained by the aforementioned method to a fluorine-containing cyclopropane monoester salt of the general formula [9] by reaction with an amine and purify the salt by recrystallization (as a recrystallization step).

[Cyclic Sulfuric Esterification Step]

First, the cyclic sulfuric esterification step will be explained below. In the cyclic sulfuric esterification step, the fluorine-containing sulfate of the general formula [2] is formed with the use of the fluorine-containing diol compound of the general formula [1], the basic compound and sulfuryl fluoride.

In the fluorine-containing diol compound of the general formula [1], $R_f$ is a $C_1$-$C_6$ linear or branched fluoroalkyl group having at least one fluorine atom. Specific examples of the fluoroalkyl group are trifluoromethyl, pentafluoroethyl, heptafluoropropyl, nonafluorobutyl, difluoromethyl, 1,1-difluoroethyl, 2,2-difluoroethyl, 1,1-difluoropropyl, 2,2-difluoropropyl, 3,3-difluoropropyl, 1,1-difluorobutyl, 2,2-difluorobutyl, 3,3-difluorobutyl, 4,4-difluorobutyl, monofluoromethyl, 1-monofluoroethyl, 2-monofluoroethyl, 1-monofluoropropyl, 2-monofluoropropyl, 3-monofluoropropy, 1-monofluorobutyl, 2-monofluorobutyl, 3-monofluorobutyl and 4-monofluorobutyl. Among others, trifluoromethyl, pentafluoroethyl, heptafluoropropyl, nonafluorobutyl and dfluoromethyl are preferred. Particularly preferred are trifluoromethyl and difluoromethyl. The fluorine-containing diol compound of the general formula [1] can be produced by e.g. methods used in the after-mentioned Reference Examples 2, 7 and 11.

The basic compound used for formation of the fluorine-containing cyclic sulfate of the general formula [2] is an alkali metal hydride, alkaline earth metal hydride, alkali metal hydroxide, alkaline earth metal hydroxide, alkali metal carbonate, alkaline earth metal carbonate, alkali metal hydrogencarbonate or alkaline earth metal hydrogencarbonate. The basic compound is preferably an alkali metal hydride, alkali metal hydroxide, alkali metal carbonate, alkali metal hydrogencarbonate, alkaline earth metal carbonate or alkaline earth metal hydrogencarbonate. More preferably, the basic compound is an alkali metal hydride, alkali metal carbonate or alkali metal hydrogencarbonate. Specific examples of the basic compound are lithium hydride, sodium hydride, potassium hydride, rubidium hydride, cesium hydride, magnesium hydride, calcium hydride, lithium hydroxide, sodium hydroxide, potassium hydroxide, rubidium hydroxide, cesium hydroxide, magnesium hydroxide, calcium hydroxide, lithium carbonate, sodium carbonate, potassium carbonate, rubidium carbonate, cesium carbonate, magnesium carbonate, calcium carbonate, lithium hydrogencarbonate, sodium hydrogencarbonate, potassium hydrogencarbonate, rubidium hydrogencarbonate, cesium hydrogencarbontate, magnesium hydrogencarbonate and calcium hydrogencarbonate. Among others, lithium hydride, sodium hydride, potassium hydride, lithium hydroxide, sodium hydroxide, potassium hydroxide, rubidium hydroxide, cesium hydroxide, sodium carbonate, potassium carbonate, rubidium carbonate, cesium carbonate, calcium carbonate, sodium hydrogencarbonate, potassium hydrogencarbonate, rubidium hydrogencarbonate, cesium hydrogencarbonate, magnesium hydrogencarbonate and calcium hydrogencarbonate are preferred. Particularly preferred are sodium hydride, potassium carbonate, cesium carbonate, potassium hydrogencarbonate and cesium hydrogencarbonate.

At the time of reacting the fluorine-containing diol compound with the sulfuryl fluoride in the presence of the basic compound, there is no particular limitation on the order of charging of these reagents. It is preferable to e.g. prepare a reaction solution by putting the fluorine-containing diol compound, the basic compound and a reaction solvent into a reaction vessel and stirring the resulting mixture, and then, introduce the sulfuryl fluoride into the reaction solution as in the after-mentioned working examples. There is no particular limitation on the reaction temperature for preparation of the reaction solution containing the fluorine-containing diol compound and the basic compound. The reaction temperature is generally −70 to 50° C., preferably −50 to 40° C., more preferably −30 to 30° C. When the reaction temperature is lower than −70° C., the reaction rate becomes slow so that it is difficult to industrially apply this reaction step.

There is no particular limitation on the reaction time for preparation of the reaction solution containing the fluorine-containing diol compound and the basic compound. It is generally preferable to, after the reaction of the two raw material compounds, determine the time at which almost all the fluorine-containing diol compound has disappeared as the end of the reaction while monitoring the progress of the reaction by any analytical means such as gas chromatography, liquid chromatography or NMR.

As the reaction solvent, there can be used a polar aprotic solvent in this reaction step. The reaction solvent is preferably an ether solvent, nitrile solvent, amide solvent, ester solvent or sulfur-containing solvent. More preferably, the reaction solvent is a nitrile solvent. Specific examples of the reaction solvent are diethyl ether, diisopropyl ether, dibutyl ether, t-butyl methyl ether, cyclopentyl methyl ether, tetrahydrofuran, acetonitrile, propionitrile, dimethylformamide, methyl acetate, ethyl acetate, propyl acetate, t-butyl acetate, dimethyl sulfoxide and sulfolane. Among others, diisopropyl ether, dibutyl ether, methyl t-butyl ether, cyclopentyl methyl ether, tetrahydrofuran, acetonitrile, propionitrile, dimethylformamide, ethyl acetate and dimethyl sulfoxide are preferred. Particularly preferred is acetonitrile. These solvents can be used solely or in combination of two or more thereof.

There is no particular limitation on the temperature of the reaction between the sulfuryl fluoride and the reaction solution containing the fluorine-containing diol compound and the basic compound. The reaction temperature is generally −50 to +50° C., preferably −40 to +40° C., more preferably −30 to +30° C. When the reaction temperature is lower than −50° C., the reaction rate becomes slow so that it is difficult to industrially apply this reaction step. When the reaction temperature is higher than 50° C., there unfavorably occurs an increased amount of impurity due to the occurrence of side reaction.

The pressure conditions of the reaction between the sulfuryl fluoride and the reaction solution is generally 0.001 to 2.0 MPa, preferably 0.001 to 1.5 MPa, more preferably 0.001 to 1.0 MPa. When the reaction pressure is too low, the reaction rate becomes slow so that it is difficult to industrially apply this reaction step. Herein, the pressure refers to an absolute pressure. The amount of the sulfuryl fluoride used is generally 0.7 to 4.0 equivalents, preferably 1 to 3.0 equivalents, more preferably 1 to 2.0 equivalents, per equivalent of the fluorine-containing diol compound. When the amount of the sulfuryl fluoride used is less than 0.7 equivalent, there may arise an adverse effect on the yield of the reaction product. When the amount of the sulfuryl fluoride used is more than 4.0 equivalents, there may arise an adverse effect on the selectivity of the reaction.

The sulfuryl fluoride can be introduced by blowing the sulfuryl fluoride into the reaction solution through a dip tube, or can be introduced to a sealable autoclave reactor.

There is no particular limitation on the time of the reaction between the sulfuryl fluoride and the reaction solution. It is preferable to, after the introduction of the sulfuryl fluoride, determine the time at which there occurs no change in the amount of the reaction product as the end of the reaction while monitoring the progress of the reaction by any analytical means such as gas chromatography, liquid chromatography or NMR.

In this reaction step, there can be used a reaction vessel made of stainless steel, Monel™, Hastelloy™, nickel etc. or a reaction vessel having a lining of the aforementioned metal material or fluoro resin such as polytetrafluoroethylene or perfluoropolyether resin.

The fluorine-containing cyclic sulfate of the general formula [2] is obtained by ordinary post-treatment operation for organic synthesis. The thus-obtained crude product can be purified to a higher purity, as required, by treatment with activated carbon, fractional distillation, column chromatography etc.

After the formation reaction of the fluorine-containing cyclic sulfate, the target compound may be isolated from the reaction solution. Alternatively, the reaction solution immediately after the reaction may be used for the subsequent cyclopropanation step as in the after-mentioned working examples. It is a preferable embodiment of the cyclic sulfuric esterification step to adopt such a procedure in view of the advantage in operability.

By carrying out the cyclic sulfuric esterification step of the present invention, it is feasible to form a fluorine-containing cyclic sulfate of the formula [13]. (This sulfate is a useful compound that can be converted to various difluoromethyl-containing compounds.)

[13]

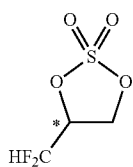

[Cyclopropanation Step]

Next, the cyclopropanation step will be explained below. In the cyclopropanation step, the fluorine-containing cyclopropane diester of the general formula [5] is formed by reacting the fluorine-containing sulfate obtained in the preceding reaction step (cyclic sulfuric esterification step) with the malonic diester of the general formula [3] in the presence of the inorganic base. The detailed scheme of the cyclopropanation step is indicated below.

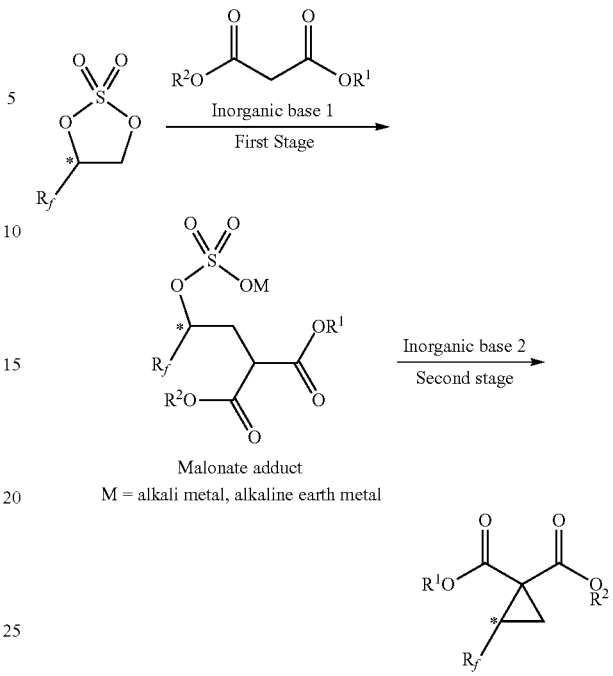

Malonate adduct
M = alkali metal, alkaline earth metal

In the cyclopropanation step, the fluorine-containing cyclopropane diester can be formed by conversion of the sulfate to an intermediate (that is, a malonate adduct) and cyclization of the malonate adduct in the reaction system as indicated in the above scheme. For detail explanation of the cyclopropanation step, these reaction stages are referred to as "first stage" and "second stage"; and the inorganic bases used in the respective stages are referred to as "inorganic base 1" and "inorganic base 2". It is one embodiment to perform the cyclopropanation step in stages. Needless to say, this embodiment is included in the present invention.

In the malonic diester of the general formula [3], each of $R^1$ and $R^2$ is a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group. Herein, the substituted alkyl group refers to a group obtained by substituting a hydrogen atom on any carbon of the alkyl group with a substituent such as halogen atom or aromatic ring group; and the substituted aromatic ring group refers to a group obtained by substituting a hydrogen atom on any carbon of the aromatic ring group with a substituent such as halogen atom, aromatic ring group, nitro group or $C_1$-$C_6$ alkoxy group. Specific examples of $R^1$, $R^2$ are methyl, ethyl, propyl, isopropyl, 1-butyl, 2-butyl, isobutyl, tert-butyl, 1-pentyl, 2-pentyl, 3-pentyl, 2-methyl-1-butyl, 2-methyl-2-butyl, 3-methyl-1-butyl, 3-methyl-2-butyl, neopentyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl, 2-ethyl-1-butyl, 1-heptyl, 1-octyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl, 1-cyclopropyl, 1-cyclopentyl, 1-cyclohexyl, benzyl, 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 1-phenylethyl, 2-phenylethyl, phenyl, naphthyl, anthracenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-nitrophenyl, 3-nirtrophenyl, 4-nirtrophenyl, 2-methoxyphenyl, 3-methoxyphenyl and 4-methoxyphenyl. Among others, methyl, ethyl, propyl, isopropyl, 1-butyl, 2-butyl, isobutyl, tert-butyl, 1-pentyl, 1-hexyl, 1-heptyl, 1-octyl, 1-nonyl, 1-decyl, 1-cyclohexyl, benzyl, phenyl and naphthyl are preferred. Particularly preferred are methyl, ethyl, propyl, isopropyl, 1-butyl, isobutyl, tert-butyl, 1-cyclohexyl, benzyl and phenyl.

Preferred examples of the malonic diester of the general formula [3] are dimethyl malonate, diethyl malonate, dipropyl malonate, diisopropyl malonate, dibutyl malonate, di-2-butyl malonate, diisobutyl malonate, di-tert-butyl malonate, dipentyl malonate, dihexyl malonate, diheptyl malonate, dioctyl malonate, dinonyl malonate, didecyl malonate, dicyclohexyl malonate, dibenzyl malonate, diphenyl malonate and dinaphthyl malonate. Among others, dimethyl malonate, diethyl malonate, dipropyl malonate, diisopropyl malonate, dibutyl malonate, diisobutyl malonate, di-tert-butyl malonate, dicyclohexyl malonate, dibenzyl malonate and dihenyl malonate are particularly preferred.

The malonic diester of the general formula [3] is used in an amount of generally 1 to 5 equivalents, preferably 1 to 3 equivalents, more preferably 1 to 1.5 equivalents, per equivalent of the fluorine-containing cyclic sulfate. When the amount of the malonic diester used is less than 1 equivalent, the yield of the reaction product may become lowered. When the amount of the malonic diester used exceeds 5 equivalents, the malonic diester remains as an impurity so that the chemical yield of the reaction product may become low.

The inorganic base used in this reaction step (which corresponds to "inorganic base 1" and "inorganic base 2" in the above scheme) is an alkali metal, alkali metal hydride, alkaline earth metal hydride, alkali metal hydroxide or alkaline earth metal hydroxide. The inorganic base is preferably an alkali metal or alkali metal hydride. Specific examples of the inorganic base are lithium, sodium, potassium, lithium hydride, sodium hydride, potassium hydride, rubidium hydride, cesium hydride, magnesium hydride, calcium hydride, lithium hydroxide, sodium hydroxide, potassium hydroxide, magnesium hydroxide and calcium hydroxide. Among others, lithium, sodium, lithium hydride, sodium hydride and potassium hydride are preferred. Particularly preferred are sodium and sodium hydride. The inorganic bases used in the respective reaction stages can be the same or different.

The amount of the inorganic base used is generally 2 equivalents or more per equivalent of the malonic diester of the general formula [3]. When the amount of the inorganic base used is less than 2 equivalent, the yield of the reaction product may become lowered. The inorganic base can be added through the first and second stages as indicated in the above scheme such that the total amount of the inorganic base 1 added in the first stage and the inorganic base 2 added in the second stage is 2 equivalents or more.

As the reaction solvent, there can be used an ether solvent, an amide solvent, an aliphatic hydrocarbon solvent or an aromatic hydrocarbon solvent in this reaction step. Specific examples of the reaction solvent are diethyl ether, diisopropyl ether, dibutyl ether, methyl tert-butyl ether, tetrahydrofuran, 2-methyltetrahydrofuran, cyclopentyl methyl ether, dimethoxyethane, dimethylformamide, dimethylacetamide, n-hexane, cyclohexane, n-heptane, n-nonane, n-octane, toluene and xylene. Among others, diethyl ether, diisopropyl ether, methyl tert-butyl ether, tetrahydrofuran, cyclopentyl methyl ether, dimethoxyethane, dimethylformamide, n-hexane, n-heptane, toluene and xylene are preferred. Particularly preferred are diisopropyl ether, methyl tert-butyl ether, tetrahydrofuran, dimethoxyethane, dimethylformamide, n-heptane and toluene. These reaction solvents can be used even in the case where this reaction step is performed through the first and second stages as indicated in the above scheme. Further, these reaction solvents can be used solely or in combination of two or more thereof.

In a preferable embodiment of the cyclopropanation step, the fluorine-containing cyclic sulfate is reacted with the malonic diester in the presence of the inorganic base. There is no particular limitation on the procedure for performing the cyclopropanation step. It is preferable to finish the reaction at the time when the raw material has almost disappeared while monitoring the progress of the reaction by any analytical means such as gas chromatography or NMR. For example, the cyclopropanation step can be performed through the first and second stages as indicated in the above scheme by, after adding the inorganic base 1 in the first stage, monitoring the progress of the reaction by analytical means such as gas chromatography or NMR, and then, adding the inorganic base 2 and/or the reaction solvent into the reaction system at the time when the formation of the malonate adduct as the intermediate has been confirmed with disappearance of almost all the fluorine-containing cyclic sulfate as the raw material or with no change in the rate of conversion of the fluorine-containing cyclic sulfate.

Alternatively, the inorganic base 1 may be excessively added in the first stage so that the unreacted inorganic acid content remaining after the first stage serves as the inorganic base 2. In this case, the equivalent amount of the inorganic base 2 used is determined as a guide by subtracting the excess amount of the inorganic base 1 from the total equivalent amount of the inorganic base 1 used. The inorganic base may be separately added as required.

In this reaction step, the reaction proceeds in a temperature range of generally −80 to 170° C., preferably −50 to 120° C., more preferably −30 to 100° C. In the case where this reaction step is performed through the first and second stages as indicated in the above scheme, the preferable range of the reaction temperature is as follows.

The temperature of the reaction in the first stage is generally −70° C. or higher, preferably −50 to 40° C., more preferably −30 to 30° C. It is preferable to shift from the first stage to the second stage at the time when the raw material has almost disappeared or the progress of the reaction stops as the end of the reaction while monitoring the progress of the reaction by analytical means such as gas chromatography or NMR. In the first stage, a large amount of solid precipitate is formed with the progress of the reaction. Thus, the concentration of the reaction solution is preferably adjusted to within the range of 0.1 to 2 M, more preferably 0.2 to 1.5 M. When the concentration of the reaction solution is higher than 2 M, it becomes difficult to stir the reaction solution. When the concentration of the reaction solution is lower than 0.1 M, there will occur a significant decrease in productivity. In the second stage, the reaction is started by raising the temperature of the reaction solution. The temperature of the reaction in the second stage is generally about 40 to 150° C., preferably 40 to 120° C., more preferably 50 to 100° C. When the reaction temperature is lower than 40° C., the cyclization is unlikely to proceed and thus requires a long time. When the reaction temperature is higher than 150° C., the cyclization itself proceeds. Under such high reaction-temperature conditions, however, there arises a possibility of the occurrence of side reaction by decomposition of the reaction product. With the progress of the reaction in the second stage, the solid precipitate gradually disappears so that it becomes easy to stir the reaction solution.

There is no particular limitation on the order of charging of the reagents in this reaction step. It is preferable to first put the reaction solvent and the inorganic base into the reaction system, prepare a mixed solution of the inorganic base in the reaction solvent, and then, add the malonic diester and the fluorine-containing cyclic sulfate as the raw material compounds to the mixed solution as in e.g. the after-mentioned working examples. At this time, the malonic diester and the fluorine-containing cyclic sulfate may be mixed together and added as a mixture into the previously prepared mixed solution. The malonic diester and the fluorine-containing cyclic sulfate may alternatively be added separately without being mixed together.

Alternatively, a solution of the malonic diester and/or the fluorine-containing cyclic sulfate may be prepared as appropriate with the addition of the reactions solvent and dropped into the previously prepared mixed solution. The order of the charging of the reagents is set as appropriate by those skilled in the art.

In the case where the malonic diester and the fluorine-containing cyclic sulfate are mixed together and introduced as the mixture, the time of introduction of the malonic diester and the fluorine-containing cyclic sulfate into the reaction system is generally 30 minutes to 48 hours, preferably 40 minutes to 24 hours, more preferably 1 to 12 hours. When the introduction time is shorter than 30 minutes, a large amount of solid precipitate will be formed rapidly. When the introduction time is longer than 48 hours, there may occur a decrease in productivity.

[Hydrolysis Step]

The hydrolysis step will be next explained below. In the hydrolysis step, the fluorine-containing cyclopropane monoester of the general formula [7] is formed by hydrolyzing the fluorine-containing cyclopropane diester obtained in the preceding reaction step.

The base used for hydrolysis of the fluorine-containing cyclopropane diester of the general formula [5] is an alkali metal hydroxide, alkaline earth metal hydroxide, alkali metal carbonate, alkaline earth metal carbonate, alkali metal hydrogencarbonate, alkaline earth metal hydrogen carbonate or a quaternary ammonium hydroxide of the general formula [6]. (These base compounds are also simply referred to as "base".)

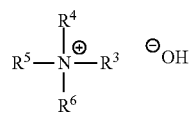

[6]

In the general formula [6], each of $R^3$, $R^4$, $R^5$ and $R^6$ is a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group. Herein, the substituted alkyl group refers to a group obtained by substituting a hydrogen atom on any carbon of the alkyl group with a substituent such as halogen atom, aromatic ring group or hydroxy group; and the substituted aromatic ring group refers to a group obtained by substituting a hydrogen atom on any carbon of the aromatic ring group with a substituent such as halogen atom, aromatic ring group, nitro group or $C_1$-$C_6$ alkoxy group. Two or more of $R^3$, $R^4$, $R^5$ and $R^6$ may form a part of the same aliphatic ring or aliphatic aromatic ring The base is preferably an alkali metal hydroxide, alkali metal carbonate, alkali metal hydrogencarbonate or quaternary ammonium hydroxide. More preferably, the base is an alkali metal hydroxide or quaternary ammonium hydroxide. Specific examples of the base are lithium hydroxide, sodium hydroxide, potassium hydroxide, rubidium hydroxide, cesium hydroxide, magnesium hydroxide, calcium hydroxide, lithium carbonate, sodium carbonate, potassium carbonate, rubidium carbonate, cesium carbonate, magnesium carbonate, calcium carbonate, lithium hydrogencarbonate, sodium hydrogencarbonate, potassium hydrogencarbonate, rubidium hydrogencarbonate, cesium hydrogencarbonate, magnesium hydrogencarbonate, calcium hydrogencarbonate, tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraheptylammonium hydroxide, dimethyldioctylammonium hydroxide, trioctylmethylammonium hydroxide, tetraoctylammonium hydroxide, decyltrimethylammonium hydroxide, dodecyltrimethylammonium hydroxide, dilauryldimethylammonium hydroxide, dimethyldioctadecylammonium hydroxide, benzyltrimethylammonium hydroxide, benzyltriethylammonium hydroxide, benzyltripropylammonium hydroxide, benzyltributylammonium hydroxide, benzyltriheptylammonium hydroxide, benzyltrihexylammonium hydroxide, benzyltriheptylammonium hydroxide, benzyltrioctylammonium hydroxide, trimethylphenylammonium hydroxide, triethylphenylammonium hydroxide, tripropylphenylammonium hydroxide, tributylphenylammonium hydroxide, tripentylphenylammonium hydroxide, trihexylphenylammonium hydroxide, triheptylphenylammonium hydroxide, trioctylphenylammonium hydroxide, dimethylpiperidinium hydroxide, ethyl-methyl piperidinium hydroxide, methyl-propyl piperidinium hydroxide, butyl-methyl piperidinium hydroxide, diethyl piperidinium hydroxide, ethyl-propyl piperidinium hydroxide, butyl-ethyl piperidinium hydroxide, dipropyl piperidinium hydroxide, butyl-propyl piperidinium hydroxide, dibutyl piperidinium hydroxide, 2-hydroxyethyltrimethylammonium hydroxide and tris(2-hydroxyethyl)methylammonium hydroxide. Among others, lithium hydroxide, sodium hydroxide, potassium hydroxide, rubidium hydroxide, cesium hydroxide, sodium carbonate, potassium carbonate, rubidium carbonate, cesium carbonate, calcium carbonate, sodium hydrogencarbonate, potassium hydrogencarbonate, rubidium hydrogencarbonate, cesium hydrogencarbonate, tetramethylammonium hydroxide, tetraethylammonium hydroxide, tetrabutylammonium hydroxide, tetrahexylammonium hydroxide, benzyltrimethylammonium hydroxide, benzyltriethylammonium hydroxide, trimethylphenylammonium hydroxide, triethylphenylammonium hydroxide, butyl-methyl piperidinium hydroxide and 2-hydroxyethyltrimethylammonium hydroxide are preferred. Particularly preferred are sodium hydroxide, potassium hydroxide, sodium carbonate, potassium carbonate, tetramethylammonium hydroxide, tetraethylammonium hydroxide and 2-hydroxyethyltrimethylammonium hydroxide.

The temperature of the hydrolysis reaction is generally −30 to +40° C., preferably −20 to +30° C., more preferably −10 to +20° C. When the reaction temperature is lower than −30° C., the hydrolysis reaction may become slow. When the reaction temperature exceeds 40° C., it is likely that there will occur side reaction.

The amount of the base used is generally 1 to 5 equivalents, preferably 1 to 3 equivalents, more preferably 1 to 2 equivalents. When the amount of the base used is less than 1 equivalent, the yield of the reaction product may become lowered. When the amount of the base used exceeds 5 equivalents, there may occur side reaction such as hydrolysis of two ester moieties of the fluorine-containing cyclopropane diester.

As the reaction solvent, there can be used water, alcohol solvent etc. in this reaction step. Specific examples of the reaction solvent are water, methanol, ethanol, propanol, isopropanol and butanol. Among others, water, methanol, ethanol, propanol and isopropanol are preferred. Particularly preferred are water, methanol and ethanol. These reaction solvents can be used solely or in combination of two or more thereof.

In the hydrolysis reaction of the fluorine-containing cyclopropane diester, one of two ester moieties located sterically away from the $R_f$ group (i.e. located in the trans position) is preferentially hydrolyzed. For example, selective hydrolysis of similar compounds has been reported in Org. Process Res. Dev., 2011, vol. 15, p. 1207-1211. By selective hydrolysis of the fluorine-containing cyclopropane diester, the fluorine-containing cyclopropane monoester of the general formula [7] is formed with two asymmetric carbon atoms. In the case where one of the asymmetric carbon atoms located in the α-position relative to the $R_f$ group is in S-configuration, the other asymmetric carbon atom is in S- or R-configuration. In the case where one of the asymmetric carbon atoms located in the α-position relative to the $R_f$ group is in R-configuration, the other asymmetric carbon atom is in S- or R-configuration.

After the reaction, the fluorine-containing cyclopropane monoester of the general formula [7] is obtained by ordinary post-treatment operation commonly for organic synthesis, e.g., by making the reaction solution acidic with the addition of an acid and then subjecting the reaction solution to extraction. The thus-obtained crude product can be purified to a higher purity, as required, by treatment with activated carbon, fractional distillation, column chromatography etc. For extraction operation, it is necessary to add the acid and thereby make the reaction solution acid. There is no particular limitation on the acid added. Examples of the acid used are: inorganic acids such as boric acid, phosphoric acid, hydrogen chloride, hydrogen bromide, nitric acid and sulfuric acid; and organic acids such as formic acid, acetic acid, oxalic acid, benzoic acid, benzenesulfonic acid and para-toluenesulfonic acid.

[Recrystallization Step]

Finally the recrystallization step will be explained below. In the recrystallization step, the amine of the general formula [8] is added to the fluorine-containing cyclopropane monoester of the general formula [7], thereby forming the salt of the fluorine-containing cyclopropane monoester and the amine as represented by the general formula [9]; and the thus-formed salt is purified by recrystallization.

In the amine of the general formula [8], each of $R^7$, $R^8$ and $R^9$ is a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group. Herein, the substituted alkyl group refers to a group obtained by substituting a hydrogen atom on any carbon of the alkyl group with a substituent such as halogen atom, amino group, hydroxy group or aromatic ring group; and the substituted aromatic ring group refers to a group obtained by substituting a hydrogen atom on any carbon of the aromatic ring group with a substituent such as halogen atom, nitro group, $C_1$-$C_6$ alkyl group or $C_1$-$C_6$ alkoxy group. Specific examples of $R^7$, $R^8$, $R^9$ are hydrogen, methyl, ethyl, propyl, isopropyl, 1-butyl, 2-butyl, isobutyl, tert-butyl, 1-pentyl, 2-pentyl, 3-pentyl, 2-methyl-1-butyl, 2-methyl-2-butyl, 3-methyl-1-butyl, 3-methyl-2-butyl, neopentyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl, 2-ethyl-1-butyl, 1-heptyl, 1-octyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl, 1-cyclopropyl, 1-cyclopentyl, 1-cyclohexyl, chloromethyl, bromomethyl, cyanomethyl, 2-hydroxyethyl, 2-aminoethyl, 2-chloroethyl, benzyl, 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 1-phenylethyl, 2-phenylethyl, phenyl, 1-naphthyl, 2-naphthyl, 1-anthracenyl, 2-anthracenyl, 9-anthracenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-nitrophenyl, 3-nitrophenyl, 4-nitrophenyl, 2-methylphenyl, 3-methylphenyl, 4-methylphenyl, 2-methoxyphenyl, 3-methoxyphenyl and 4-methoxyphenyl. Among others, hydrogen, methyl, ethyl, 1-propyl, isopropyl, 1-butyl, 1-pentyl, 1-hexyl, 1-heptyl, 1-octyl, 1-nonyl, 1-decyl, 1-cyclohexyl, benzyl, 1-phenylethyl, 2-phenylethyl, phenyl, naphthyl, 1-(1-naphthyl)ethyl, 1-(2-naphthyl)ethyl, 2-(1-naphthyl)ethyl and 2-(2-naphthyl)ethyl are preferred. Particularly preferred are hydrogen, methyl, ethyl, propyl, isopropyl, 1-butyl, 1-cyclohexyl, benzyl, 1-phenylethyl, 2-phenylethyl, phenyl and 1-(1-naphthyl)ethyl.

The optical purity of the fluorine-containing cyclopropane monoester-amine salt of the general formula [9] is improved by recrystallization purification. For example, it has been reported in International Publication No. WO 2010/014739 that the optical purity of similar compounds can be improved by recrystallization with the use of chiral amines.

In the case where the amine of the general formula [8] has an asymmetric center in $R^7$, $R^8$, $R^9$, it is a preferable embodiment of the recrystallization step that the amine is an optically active amine for optical purity improvement by recrystallization. Namely, the amine of the general formula [10] is preferred as the amine of the general formula [8]. In this amine, each of $R^7$, $R^8$ and $R^9$ is a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group. Specific examples of $R^7$, $R^8$, $R^9$ are hydrogen, methyl, ethyl, propyl, isopropyl, 1-butyl, 2-butyl, isobutyl, tert-butyl, 1-pentyl, 2-pentyl, 3-pentyl, 2-methyl-1-butyl, 2-methyl-2-butyl, 3-methyl-1-butyl, 3-methyl-2-butyl, neopentyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2,3-dimethyl-2-butyl, 3,3-dimethyl-2-butyl, 2-ethyl-1-butyl, 1-heptyl, 1-octyl, 1-nonyl, 1-decyl, 1-undecyl, 1-dodecyl, 1-tridecyl, 1-tetradecyl, 1-pentadecyl, 1-hexadecyl, 1-heptadecyl, 1-octadecyl, 1-cyclopropyl, 1-cyclopentyl, 1-cyclohexyl, chloromethyl, bromomethyl, cyanomethyl, 2-hydroxyethyl, 2-aminoethyl, 2-chloroethyl, benzyl, 2-chlorobenzyl, 3-chlorobenzyl, 4-chlorobenzyl, 2-fluorobenzyl, 3-fluorobenzyl, 4-fluorobenzyl, 2-bromobenzyl, 3-bromobenzyl, 4-bromobenzyl, 1-phenylethyl, 2-phenylethyl, phenyl, 1-naphthyl, 2-naphthyl, 1-anthracenyl, 2-anthracenyl, 9-anthracenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-nitrophenyl, 3-nitrophenyl, 4-nitrophenyl, 2-methylphenyl, 3-methylphenyl, 4-methylphenyl, 2-methoxyphenyl, 3-methoxyphenyl and 4-methoxyphenyl. Among others, hydrogen, methyl, ethyl, propyl, isopropyl, 1-butyl, 2-butyl, isobutyl and tert-butyl are preferred. Particularly preferred are hydrogen, methyl and ethyl.

In the case where $R^{10}$ is any group other than hydrogen atom, that is, $R^{10}$ is either a $C_1$-$C_{18}$ alkyl group or substituted alkyl group having a linear or branched structure or a cyclic structure (in the case of three or more carbon atoms) or a $C_6$-$C_{18}$ aromatic ring group or substituted aromatic ring group, the amine of the general formula [10] has an asymmetric center and serves as an optically active amine to form the fluorine-containing cyclopropane monoester-amine salt.

Further, $Ar^1$ is a $C_6$-$C_{14}$ aromatic ring group or substituted aromatic ring group. Herein, the substituted aromatic ring group refers to a group obtained by substituting a hydrogen atom on any carbon of the aromatic ring group with a substituent such as halogen atom, nitro group, $C_1$-$C_6$ alkyl group or $C_1$-$C_6$ alkoxy group on any carbon atom of the aromatic ring group. Specific examples of $Ar^1$ are phenyl, 1-naphthyl, 2-naphthyl, 1-anthracenyl, 2-anthracenyl, 9-anthracenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-nitrophenyl, 3-nitrophenyl, 4-nitrophenyl, 2-methylphenyl, 3-methylphenyl, 4-methylphenyl, 2-methoxyphenyl, 3-methoxyphenyl and 4-methoxyphenyl. Among others, phenyl, 1-naphthyl, 2-naphthyl, 2-nitrophenyl, 3-nitrophenyl, 4-nitrophenyl, 2-methoxyphenyl, 3-methoxyphenyl and 4-methoxyphenyl are preferred. Particularly preferred are phenyl, 1-naphthyl and 2-naphthyl.

Specific examples of the amine of the general formula [8] are 1-phenylethylamine, 1-phenylpropylamine, 4-phenyl-2-butylamine, 2-methyl-1-phenylpropylamine, 1-(2-methylphenyl)ethylamine, 1-(3-methylphenyl)ethylamine, 1-(4-methylphenyl)ethylamine, 1-(4-ethylphenyl)ethylamine, N-methyl-1-phenylethylamine, N-methyl-1-phenylpropylamine, N-methyl-1-(4-methylphenyl)ethylamine, 1-(2-naphthyl)ethylamine, 1-(2-naphthyl)propylamine, N-methyl-1-(2-naphthyl)ethylamine, N-methyl-1-(2-naphthyl)propylamine and 1-(1-naphthyl)ethylamine. Among others, 1-phenylethylamine, 1-phenylpropylamine, 1-(4-methylphenyl)ethylamine, 1-(4-ethylphenyl)ethylamine, N-methyl-1-phenethylamine, 1-(2-naphthyl)ethylamine, 1-(2-naphthyl)propylamine and 1-(1-naphthyl)ethylamine are preferred.

In the amine of the general formula [10], the asymmetric carbon atom is marked with *. This asymmetric carbon atom is in either R- or S-configuration relative to the fluorine-containing cyclopropane monoester of the general formula [7].

As the solvent for recrystallization purification, there can be used an aliphatic hydrocarbon solvent, aromatic hydrocarbon solvent, halogenated hydrocarbon solvent, ether solvent, ketone solvent, ester solvent, nitrile solvent, alcohol solvent or water. The recrystallization solvent is preferably an aliphatic hydrocarbon solvent, halogenated hydrocarbon solvent, ether solvent, ketone solvent, ester solvent, nitrile solvent, alcohol solvent or water. More preferably, the recrystallization solvent is an aliphatic hydrocarbon solvent, ketone solvent, nitrile solvent, alcohol solvent or water. Specific examples of the recrystallization solvent are n-pentane, n-hexane, cyclohexane, n-heptane, methylcylcohexane, benzene, toluene, ethylbenzene, xylene, mesitylene, methylene chloride, chloroform, 1,2-dichloroethane, diethyl ether, diisopropyl ether, tetrahydrofuran, methyl tert-butyl ether, cyclopentyl methyl ether, acetone, methyl ethyl ketone, methyl i-butyl ketone, ethyl acetate, n-butyl acetate, acetonitrile, propionitrile, methanol, ethanol, n-propanol, isopropanol, n-butanol and isobutanol. Among others, n-hexane, methylcyclohexane, n-heptane, methylene chloride, diisopropyl ether, tetrahydrofuran, methyl tert-butyl ether, acetone, methyl ethyl ketone, ethyl acetate, acetonitrile, methanol, ethanol, n-propanol, isobutanol and water are preferred. Particularly preferred are n-hexane, methylcyclohexane, n-heptane, acetone, acetonitrile, methanol, ethanol, n-propanol, isopropanol, diisopropyl ether and water. These recrystallization solvents can be used solely or in combination of two or more thereof.

The amount of the solvent used for recrystallization purification is generally 1 ml or more, preferably 1 to 100 ml, more preferably 1 to 50 ml, per 1 g of the crude crystal of the fluorine-containing cyclopropane monoester-amine salt of the general formula [9].

In the recrystallization step, the crystal of the salt can be smoothly and efficiently precipitated with the use of a seed crystal. The amount of the seed crystal used is generally 0.0001 g or more, preferably 0.0001 to 0.1 g, more preferably 0.001 to 0.05 g, per 1 g of the crude crystal of the fluorine-containing cyclopropane monoester-amine salt of the general formula [9].

The temperature conditions of recrystallization operation can be set as appropriate depending on the boiling and freezing points of the recrystallization solvent used. In general, the recrystallization operation is performed as follows. The unpurified crude crystal of the salt is dissolved in the recrystallization solvent at a temperature from about 30° C. to the boiling point of the recrystallization solvent. The crystal is precipitated out of the solution by, while stirring the solution or leaving the solution still, gradually decreasing the temperature of the solution. The solution is finally cooled to −20° C. to room temperature (25° C.).

The chemical and optical purity of the precipitated crystal is improved by the recrystallization purification. It is thus feasible to obtain the fluorine-containing cyclopropane monoester-amine salt of the general formula [9] with high chemical and optical purity by recovering the precipitated crystal by filtration etc. Further, it is feasible to obtain the salt with higher chemical and optical purity by repeatedly performing the recrystallization operation. The unpurified crude crystal of the salt can be subjected to decolorization by dissolving the crystal in the recrystallization solvent and treating the salt with activated carbon.

The time of the purification is generally 0.1 to 120 hours. As the purification time varies depending on the purification conditions, it is preferable to determine the time at which the crystal has been recovered with high chemical and optical purity and high yield as the end of the purification while monitoring and analyzing the chemical and optical purity of the precipitated crystal and the amount of precipitation of the crystal.

The recovered crystal can be purified to a higher chemical purity by removing the solvent etc. adhered to the crystal and drying the crystal with the use of a rotary evaporator, a vibration dryer, a conical dryer, a shelf dryer etc. In general, the drying is performed under conditions of a temperature of about 30 to 100° C. and a vacuum degree of 0.0001 MPa to atmospheric pressure (0.1 MPa).

The number of times of the recrystallization operation is generally 1 to 7, preferably 1 to 5, more preferably 1 to 3. When the number of times of the recrystallization operation is small, the chemical purity of the salt may not be improved to a sufficient level. When the number of times of the recrystallization operation is too large, the yield of the crystal may become unfavorably lowered.

The raw material can be purified by recrystallization regardless of the optical purity of the raw material. The higher the optical purity of the raw material to be purified by recrystallization, the higher the efficiency of the purification. The recrystallization purification from a racemic mixture is low in efficiency. For this reason, the optical purity of the raw material to be purified by recrystallization is preferably 30% ee or higher, more preferably 70% ee or higher.

One example of the salt is a fluorine-containing cyclopropane monoester-amine salt of the general formula [17]. Herein, is a $C_1$-$C_6$ linear or branched alkyl group. Specific example of are methyl, ethyl, 1-propyl, 2-propyl, 1-butyl, 2-butyl, tert-butyl, 1-heptyl and 1-hexyl. Among others, methyl, ethyl, 1-propyl, 2-propyl, 1-butyl, 2-butyl and tert-butyl are preferred. Particularly preferred are methyl and ethyl.

$R^{12}$, $R^{13}$ and $R^{14}$ are each independently a hydrogen atom, or a $C_1$-$C_6$ linear or branched alkyl group. Specific examples of $R^{12}$, $R^{13}$, $R^{14}$ are hydrogen, methyl, ethyl, 1-propyl, 2-propyl, 1-butyl, 2-butyl, tert-butyl, 1-heptyl and 1-hexyl. Among others, hydrogen, methyl, ethyl, 1-propyl, 2-propyl, 1-butyl, 2-butyl and tert-butyl are preferred. Particularly preferred are hydrogen, methyl and ethyl.

$Ar^2$ is a $C_6$-$C_{10}$ aromatic ring group or substituted aromatic ring group. Herein, the substituted aromatic ring group refers to a group obtained by substituting a hydrogen atom on any carbon of the aromatic ring group with a substituent such as halogen atom, nitro group, $C_1$-$C_6$ alkyl group or $C_1$-$C_6$ alkoxy group on any carbon atom of the aromatic ring group. Specific examples of $Ar^2$ are phenyl, 1-naphthyl, 2-naphthyl, 1-anthracenyl, 2-anthracenyl, 9-anthracenyl, 3-chlorophenyl, 4-chlorophenyl, 2-fluorophenyl, 3-fluorophenyl, 4-fluorophenyl, 2-nitrophenyl, 3-nitrophenyl, 4-nitrophenyl, 2-methylphenyl, 3-methylphenyl, 4-methylphenyl, 2-methoxyphenyl, 3-methoxyphenyl and 4-methoxyphenyl. Among others, phenyl, 1-naphthyl, 2-naphthyl, 2-chlorophenyl, 4-chlorophenyl, 2-nitrophenyl, 4-nitrophenyl, 2-methoxyphenyl and 4-methoxyphenyl are preferred. Particularly preferred are phenyl, 1-naphthyl and 2-naphthyl.

In the case where $R^{14}$ is a $C_1$-$C_6$ linear or branched alkyl group, the amine has an asymmetric center and serves as an optically active amine to form the fluorine-containing cyclopropane monoester-amine salt.

The thus-obtained fluorine-containing cyclopropane monoester-amine salt of the general formula [9] is a useful compound as an intermediate for pharmaceutical and agrichemical products. For example, the cyclopropane monoester salt can be converted to a fluorine-containing cyclopropane amino acid compound as in Reference Example 12 by performing Curtius rearrangement or hydrolysis reaction of the monoester salt after removing an ammonium salt. The resulting amino acid compound is usable as an intermediate for production of hepatitis c virus inhibitors as reported in International Publication No. WO 2009/124987.

EXAMPLES

The present invention will be described in more detail below by way of the following examples. These examples are not intended to limit the present invention thereto. Herein, the unit "%" of analytical values means area % of respective compositions as measured with a nuclear magnetic resonance spectrometer (NMR) or a gas-chromatograph mass spectrometer.

Example 1

Into a 200-ml stainless steel autoclave reactor, acetonitrile (100 ml), 3,3-difluoro-1,2-propanediol of the following formula (as a racemic mixture, purity: 96.6 wt %, 11.6 g, 100 mmol) and potassium carbonate (15.2 g, 110 mmol) were put. The contents of the reactor were stirred for 1 hour at room temperature.

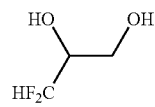

The reactor was cooled to −10° C. Next, sulfuryl fluoride (16.6 g, 163 mmol) was gradually introduced into the reactor. At this time, the inside temperature of the reactor was −5 to 2° C. After the completion of the introduction of the sulfuryl fluoride, the contents of the reactor were stirred for 2.5 hours while the inside temperature of the reactor was set to −5 to 0° C. Subsequently, the inside temperature of the reactor was raised to room temperature over 30 minutes. The thus-obtained reaction solution was analyzed by $^{19}$F-NMR. It was found that the target fluorine-containing cyclic sulfate was obtained. The content of the target sulfate was 69.45 mmol. The yield of the target sulfate was 69.4%. The reaction solution was subjected to suction filtration so as to remove a solid precipitate. The filtrate was concentrated by a rotary evaporator. The concentration residue was treated by column chromatography. As a result, the target fluorine-containing cyclic sulfate of the following formula was obtained. The content of the target sulfate was 58.3 mmol. The yield of the target sulfate was 58.2%.

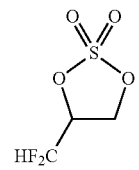

The NMR data of the target sulfate was as follows: $^1$H-NMR (deuterated solvent: CD$_3$CN, reference material: tetramethylsilane) δ ppm: 4.89 (dq, 2H), 5.25 (m, 1H), 6.19 (dt, 1H); $^{19}$F-NMR (deuterated solvent: CD$_3$CN, reference material: hexafluorobenzene set as −162.2 ppm) −131.9 (ddd, 1F), −130.6 (ddd, 1F).

Example 2

Provided was a 200-ml three-neck flask with a thermometer well, a Dimroth condenser and a septum. After the inside of the flask was replaced by nitrogen, dimethoxyethane (31.2 ml) and sodium hydride (3.93 g, 98.3 mmol)

were put into the flask. The flask was cooled by ice water. Next, a mixture of diethyl malonate (7.49 g, 46.8 mmol) and dimethoxyethane (31.2 ml) was gradually dropped into the flask over 10 minutes. At this time, the inside temperature of the flask was 2 to 14° C. After the completion of the dropping, the contents of the flask were stirred for 30 minutes while the flask was kept cooled by ice water. Subsequently, a mixture of a fluorine-containing cyclic sulfate of the following formula (8.48 g, 41.3 mmol), dimethoxyethane (31.2 ml) and benzotrifluoride (1.50 g, 10.27 mmol) as an internal standard material was gradually dropped into the flask over 5 minutes.

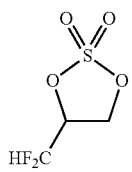

At this time, the inside temperature of the flask was 3 to 17° C. After the completion of the dropping, the contents of the flask were stirred for 30 minutes while the flask was kept cooled by ice water. The flask was heated in an oil bath to an inside temperature of about 80° C. The contents of the flask were then stirred for 2.5 hours. After the heating and stirring, the flask was cooled to room temperature. The thus-obtained reaction solution was subjected to solvent evaporation and concentration by a rotary evaporator until the weight of the solution became 29.3 g. The concentrated solution was diluted with 93.6 ml of diisopropyl ether. The diluted solution was gradually dropped into a cooled liquid mixture of sulfuric acid (0.73 g, 7.4 mmol) and water (119 ml). At this time, the inside temperature was 5 to 7° C. The resulting mixture was separated into two layers. The aqueous layer was extracted with diisopropyl ether (78 ml×2). All the extracted organic layers were combined into one and concentrated by a rotary evaporator. The concentration residue was treated by column chromatography. As a result, the target fluorine-containing cyclopropane diester of the following formula was obtained in an amount of 8.85 g (content: 22.0 mmol). The yield of the target diester was 53%.

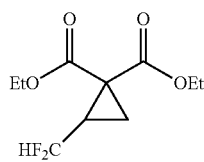

The NMR data of the target diester was as follows: $^1$H-NMR (deuterated solvent: deuterated chloroform, reference material: tetramethylsilane) δ ppm: 1.29 (td, 6H), 1.54 (m, 1H), 1.75 (m, 1H), 2.35 (m, 1H), 4.23 (m, 4H), 5.72 (td, 1H); $^{19}$F-NMR (deuterated solvent: deuterated chloroform, reference material: hexafluorobenzene set as −162.2 ppm) −117.8 (ddd, 1F), −111.6 (ddd, 1F).

Example 3

Into a 50-ml stainless steel autoclave reactor, THF (17 ml) and sodium hydride (0.89 g, 22.3 mmol) were put. The reactor was cooled by ice water. Next, 3,3-difluoro-1,2-propanediol of the following formula (as a racemic mixture, 1.0 g, 8.9 mmol) was added little by little into the reactor.

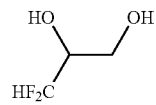

After the addition, a lid was put on the reactor. The contents of the reactor were then stirred for 20 minutes while the reactor was kept cooled by ice water. Subsequently, the reactor was cooled by the use of a dry ice-acetonitrile mixture (−45° C.). The inside of the reactor was vacuumed to about 0.001 MPa by a vacuum pump. After that, sulfuryl fluoride (1.1 g, 10.8 mmol) was gradually introduced into the reactor over 1 hour. The inside pressure of the reactor was increased to 0.2 MPa during the introduction. After the completion of the introduction, the contents of the reactor were stirred for 2 hours while the reactor was kept cooled. The contents of the reactor were further stirred overnight at room temperature. The thus-obtained reaction solution was analyzed by $^{19}$F-NMR. It was found that the target fluorine-containing cyclic sulfate of the following formula was obtained. The content of the target sulfate was 4.5 mmol. The yield of the target sulfate was 50.7%.

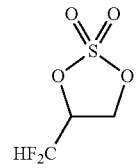

Example 4

Into a 50-ml three-neck flask with a thermometer well, a Dimroth condenser and a septum, diethyl malonate (0.80 g, 5.0 mmol) and THF (13 ml) were put. The flask was cooled by ice water. Next, sodium hydride (0.45 g, 11.3 mmol) was added little by little into the flask. At this time, the inside temperature of the flask was 8 to 9° C. After the addition, a dropping funnel was attached to the flask. The reaction solution obtained in Example 3, in which the fluorine-containing cyclic sulfate of the following formula was contained, was gradually dropped into the flask through the dropping funnel.

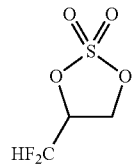

At this time, the inside temperature of the flask was 3 to 7° C. While the flask was kept cooled by ice water, the contents of the flask were stirred for 2 hours. The thus-obtained reaction solution was reacted for 1 hour while the flask was heated in an oil bath to an inside temperature of about 68.8° C. (that is, the reaction was performed under reflux conditions). The reaction solution was subjected to filtration. The filtered solid precipitate was washed with 15 ml of diisopropyl ether. The filtrate and the washing liquid were combined into one and concentrated by a rotary evaporator. As a result, a crude product of the target fluorine-containing cyclopropane diester of the following formula was obtained in an amount of 5.3 g (content: 2.4 mmol). The yield of the target diester was 54%.

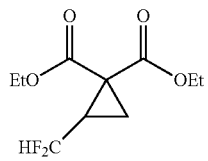

Example 5

Into a 200-ml stainless steel autoclave reactor, acetonitrile (100 ml), (S)-3,3-difluoro-1,2-propanediol of the following formula (chemical purity: 91.6 wt %, optical purity: 82.0% ee, 12.2 g, 100 mmol) and potassium carbonate (16.6 g, 120 mmol) were put. The contents of the reactor were stirred for 1 hour at room temperature.

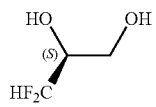

The reactor was cooled to an inside temperature of −5° C. Next, sulfuryl fluoride (14.9 g, 146 mmol) was gradually introduced into the reactor. At this time, the inside temperature of the reactor was −5 to 4° C. After the completion of the introduction of the sulfuryl fluoride, the contents of the reactor were stirred for 3 hours while the inside temperature of the reactor was set to −5 to 0° C. Subsequently, the inside temperature of the reactor was raised to room temperature over 15 minutes. The thus-obtained reaction solution was analyzed by $^{19}$F-NMR. It was found that the target fluorine-containing cyclic sulfate of the following formula was obtained. The content of the target sulfate was 77.1 mmol. The yield of the target sulfate was 77.1%.

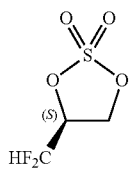

The reaction solution was subjected to suction filtration so as to remove a solid precipitate. The filtered precipitate was washed with 30 ml of toluene. The filtrate and the washing liquid were combined into one and concentrated by a rotary evaporator. The concentration residue was subjected to extraction with the addition of 65 ml of toluene and 39 ml of water. The resulting mixture was separated into two layers. The aqueous layer was again extracted with 26 ml of toluene. The extracted organic layers were combined into one and subjected to concentration and azeotropic dehydration. As a result, the target fluorine-containing cyclic sulfate was obtained in an amount of 12.8 g. The content of the target sulfate was 65.4 mmol. The yield of the target sulfate was 65.4%. The NMR data of the target sulfate was as follows: $^1$H-NMR (deuterated solvent: CD$_3$CN, reference material: tetramethylsilane) δ ppm: 4.89 (dq, 2H), 5.25 (m, 1H), 6.19 (dt, 1H); $^{19}$F-NMR (deuterated solvent: CD$_3$CN, reference material: hexafluorobenzene set as −162.2 ppm) −131.9 (ddd, 1F), −130.6 (ddd, 1F).

Example 6

Provided was a 200-ml three-neck flask with a thermometer well, a Dimroth condenser and a septum. After the inside of the flask was replaced by nitrogen, THF (25 ml) and sodium hydride (2.25 g, 56.2 mmol) was put into the flask. The flask was cooled by ice water. Next, a mixture of diethyl malonate (4.09 g, 25.6 mmol) and THF (17 ml) was gradually dropped into the flask over 30 minutes. At this time, the inside temperature of the flask was 3 to 5° C. After the completion of the dropping, the contents of the flask were stirred for 30 minutes while the flask was kept cooled by ice water. Subsequently, a mixture of the fluorine-containing cyclic sulfate of the following formula (5.0 g, 25.6 mmol) obtained in Example 5, THF (9 ml) and benzotrifluoride (1.47 g, 10 mmol) as an internal standard material was gradually dropped into the flask over 30 minutes.

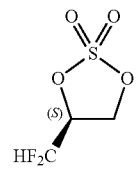

At this time, the inside temperature of the flask was 3 to 4° C. After the completion of the dropping, the contents of the flask were stirred for 3.5 hours while the flask was kept cooled by ice water. Further, THF (34 ml) was added into the flask. While the flask was heated in an oil bath to an inside temperature of about 70° C., the contents of the flask were stirred for 3 hours. After that, the flask was cooled to room temperature. The thus-obtained reaction solution was gradually dropped into a cooled liquid mixture of sulfuric acid (0.40 g, 4.1 mmol) and water (85 ml). At this time, the inside temperature was 3 to 5° C. The resulting mixture was separated into two layers. The aqueous layer was extracted with diisopropyl ether (100 ml two times and 50 ml one time). All the extracted organic layers were combined into one and concentrated by a rotary evaporator. The concentration residue was treated by column chromatography. As a result, the target fluorine-containing cyclopropane diester of the following formula was obtained in an amount of 4.5 g. The content of the target diester was 17.1 mmol. The yield of the target diester was 67%.

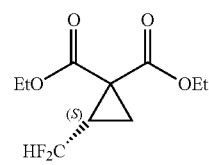

The NMR data of the target diester was as follows: $^1$H-NMR (deuterated solvent: deuterated chloroform, reference material: tetramethylsilane) δ ppm: 1.29 (td, 6H), 1.54 (m, 1H), 1.75 (m, 1H), 2.35 (m, 1H), 4.23 (m, 4H), 5.72 (td, 1H); $^{19}$F-NMR (deuterated solvent: deuterated chloroform, reference material: hexafluorobenzene set as −162.2 ppm) −117.8 (ddd, 1F), −111.6 (ddd, 1F).

Example 7

Provided was a 200-ml three-neck flask with a thermometer well, a Dimroth condenser and a septum. After the inside of the flask was replaced by nitrogen, THF (17 ml) and sodium hydride (2.87 g, 71.8 mmol) was put into the flask. The flask was cooled by ice water. Next, a mixture of dipropyl malonate (6.49 g, 34.5 mmol) and THF (19 ml) was gradually dropped into the flask over 40 minutes. At this time, the inside temperature of the flask was 4 to 5° C. After the completion of the dropping, the contents of the flask were stirred for 30 minutes while the flask was kept cooled by ice water. Subsequently, a mixture of the fluorine-containing cyclic sulfate of the following formula (5.0 g, 28.7 mmol) obtained in Example 5, THF (19 ml) and benzotrifluoride (1.46 g, 10 mmol) as an internal standard material was gradually dropped into the flask over 30 minutes.

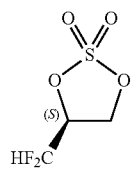

At this time, the inside temperature of the flask was 3 to 4° C. After the completion of the dropping, the contents of the flask were stirred for 1.5 hours while the flask was kept cooled by ice water. The flask was heated in an oil bath to an inside temperature of about 65° C. The contents of the flask were stirred for 1.5 hours. After that, the flask was cooled to room temperature. The thus-obtained reaction solution was gradually dropped into a cooled liquid mixture of sulfuric acid (0.89 g, 9.1 mmol) and water (57 ml). At this time, the inside temperature was 3 to 5° C. The resulting mixture was separated into two layers. To the aqueous layer, 20 ml of water was added. The aqueous layer was then extracted with 100 ml of diisopropyl ether. All the extracted organic layers were combined into one and concentrated by a rotary evaporator. The concentration residue was treated by column chromatography. As a result, the target fluorine-containing cyclopropane diester of the following formula was obtained in an amount of 6.52 g. The content of the target diester was 11.9 mmol. The yield of the target diester was 43%.

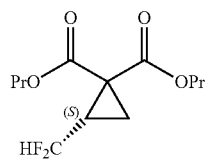

The NMR data of the target diester was as follows: $^1$H-NMR (deuterated solvent: deuterated chloroform, reference material: tetramethylsilane) δ ppm: 0.96 (t, 6H), 1.55 (m, 1H), 1.69 (m, 5H), 2.35 (m, 1H), 4.13 (q, 4H), 5.71 (td, 1H); $^{19}$F-NMR (deuterated solvent: deuterated chloroform, reference material: hexafluorobenzene set as −162.2 ppm) −117.7 (ddd, 1F), −111.5 (ddd, 1F).

Example 8

Into a 200-ml stainless steel autoclave reactor, acetonitrile (100 ml), (R)-3,3-difluoro-1,2-propanediol of the following formula (chemical purity: 89.5 wt %, optical purity: 78.2% ee, 12.5 g, 100 mmol) and potassium carbonate (16.6 g, 120 mmol) were put. The contents of the reactor were stirred for 1 hour at room temperature.

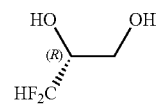

The reactor was cooled by a coolant of −10° C. Next, sulfuryl fluoride (14.2 g, 139 mmol) was gradually introduced into the reactor. At this time, the inside temperature of the reactor was −10 to 5° C. After the completion of the introduction of the sulfuryl fluoride, the contents of the reactor were stirred for 3 hours while the inside temperature of the reactor was set to −5 to 0° C. Subsequently, the inside temperature of the reactor was raised to room temperature over 30 minutes. The thus-obtained reaction solution was analyzed by $^{19}$F-NMR. It was found that the target fluorine-containing cyclic sulfate of the following formula was obtained. The content of the target sulfate was 74.2 mmol. The yield of the target sulfate was 74.2%.

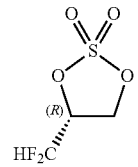

The reaction solution was cooled to 0° C. and subjected to suction filtration so as to remove a solid precipitate. The filtered precipitate was washed with 30 ml of toluene. The filtrate and the washing liquid were combined into one and concentrated by a rotary evaporator. The concentration residue was subjected to extraction with the addition of 100 ml of toluene and 50 ml of water. The resulting mixture was separated into two layers. The aqueous layer was again extracted with 20 ml of toluene. The extracted organic layers were combined into one and subjected to concentration and azeotropic dehydration. As a result, a crude product of the target fluorine-containing cyclic sulfate was obtained in an amount of 13.0 g. The content of the target sulfate was 87.8 wt %, 65.5 mmol. The yield of the target sulfate was 65.5%. The NMR data of the target sulfate was as follows: $^1$H-NMR (deuterated solvent: CD$_3$CN, reference material: tetramethylsilane) δ ppm: 4.89 (dq, 2H), 5.25 (m, 1H), 6.19 (dt, 1H); $^{19}$F-NMR (deuterated solvent: CD$_3$CN, reference material: hexafluorobenzene set as −162.2 ppm) −131.9 (ddd, 1F), −130.6 (ddd, 1F).

Example 9

Into a stainless steel autoclave reactor, acetonitrile (850 ml), (R)-3,3-difluoro-1,2-propanediol of the following formula (chemical purity: 95.2 wt %, optical purity: 89.7% ee, 100.1 g, 850 mmol) and potassium carbonate (141 g, 1020 mmol) were put. The contents of the reactor were stirred for 1 hour at room temperature.

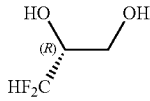

The reactor was cooled by a coolant of −10° C. Next, sulfuryl fluoride (104.1 g, 1020 mmol) was gradually introduced into the reactor. At this time, the inside temperature of the reactor was −7 to −1° C. After the completion of the introduction of the sulfuryl fluoride, the contents of the reactor were stirred for 3 hours while the inside temperature of the reactor was set to −5 to 0° C. After that, the inside temperature of the reactor was raised to room temperature over 1 hour. The thus-obtained reaction solution was analyzed by $^{19}$F-NMR. It was found that the target fluorine-containing cyclic sulfate of the following formula was obtained. The content of the target sulfate was 638.4 mmol. The yield of the target sulfate was 75.1%.

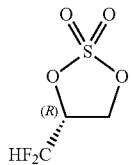

The reaction solution was cooled to 0° C. and subjected to suction filtration so as to remove a solid precipitate. The filtered precipitate was washed with 250 ml of toluene. The filtrate and the washing liquid were combined into one and concentrated by a rotary evaporator. The concentration residue was subjected to extraction with the addition of 480 ml of toluene and 240 ml of water. The resulting mixture was separated into two layers. The aqueous layer was again extracted with 120 ml of toluene. The extracted organic layers were combined into one and concentrated. Remaining water was removed from the concentrate by azeotropic dehydration with the addition of 60 ml of toluene. As a result, a crude product of the target fluorine-containing cyclic sulfate was obtained in an amount of 121.0 g. The content of the target sulfate was 94.9 wt %, 659.3 mmol. The yield of the target sulfate was 77.6%.

Example 10

Provided was a 300-ml three-neck flask with a thermometer well, a Dimroth condenser and a septum. After the inside of the flask was replaced by nitrogen, THF (55 ml) and sodium hydride (4.4 g, 110 mmol) were put into the flask. The flask was cooled by ice water. Next, a mixture of diethyl malonate (8.0 g, 50 mmol) and THF (56 ml) was gradually dropped into the flask over 40 minutes. At this time, the inside temperature of the flask was 3 to 5° C. After the completion of the dropping, the contents of the flask were stirred for 30 minutes while the flask was kept cooled by ice water. Subsequently, a mixture of the fluorine-containing cyclic sulfate of the following formula (9.9 g, 50 mmol) obtained in Example 8, THF (56 ml) and benzotri-fluoride (2.92 g, 20 mmol) as an internal standard material was gradually dropped into the flask over 30 minutes.

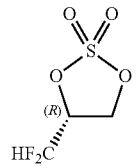

At this time, the inside temperature of the flask was 3 to 5° C. After the completion of the dropping, the contents of the flask were stirred for 1 hour while the flask was kept cooled by ice water. The flask was heated in an oil bath to an inside temperature of about 66° C. The contents of the flask were then stirred for 2.5 hours. After the heating and stirring, the flask was cooled to room temperature. The contents of the flask were further stirred overnight at room temperature. The thus-obtained reaction solution was gradually dropped into a cooled liquid mixture of sulfuric acid (0.77 g, 7.9 mmol) and water (167 ml). At this time, the inside temperature was 3 to 5° C. The resulting mixture was separated into two layers. The aqueous layer was extracted with diisopropyl ether (170 ml two times). All the extracted organic layers were combined into one and concentrated by a rotary evaporator. The concentration residue was treated by column chromatography. As a result, the target fluorine-containing cyclopropane diester of the following formula was obtained in an amount of 9.7 g. The content of the target diester was 30.3 mmol. The yield of the target diester was 62%.

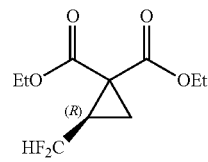

The NMR data of the target diester was as follows: $^{1}$H-NMR (deuterated solvent: deuterated chloroform, reference material: tetramethylsilane) δ ppm: 1.29 (td, 6H), 1.54 (m, 1H), 1.75 (m, 1H), 2.35 (m, 1H), 4.23 (m, 4H), 5.72 (td, 1H); $^{19}$F-NMR (deuterated solvent: deuterated chloroform, reference material: hexafluorobenzene set as −162.2 ppm) −117.8 (ddd, 1F), −111.6 (ddd, 1F).

Example 11

Provided was a 500-ml four-neck flask with a thermometer well, a Dimroth condenser, a septum and a mechanical stirrer. After the inside of the flask was replaced by nitrogen, dimethoxyethane (80 ml) and sodium hydride (10.08 g, 252 mmol) were put into the flask. The flask was cooled by ice water. Next, a mixture of diethyl malonate (8.0 g, 50 mmol) and dimethoxyethane (80 ml) was gradually dropped into the flask over 25 minutes. At this time, the inside temperature of the flask was 3 to 5° C. After the completion of the dropping, the contents of the flask were stirred for 30 minutes while the flask was kept cooled by ice water. Subsequently, a mixture of a fluorine-containing cyclic sulfate of the following formula (chemical purity: 90.77 wt %, optical purity: 77.3% ee, 23.02 g, 120 mmol), dimethoxyethane (80 ml) and benzotrifluoride (5.84 g, 40 mmol) as an internal standard material was gradually dropped into the flask over 50 minutes.

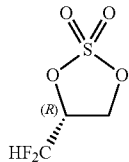

At this time, the inside temperature of the flask was 3 to 5° C. After the completion of the dropping, the contents of the flask were stirred for 1 hour while the flask was kept cooled by ice water. The flask was heated in an oil bath to an inside temperature of about 80° C. The contents of the flask were then stirred for 2 hours. After the heating and stirring, the flask was cooled to room temperature. The contents of the flask were further stirred overnight at room temperature. The thus-obtained reaction solution was concentrated by a rotary evaporator so as to remove about 170 ml of the solvent. To the concentrated solution, 240 ml of diisopropyl ether was added. This solution was gradually dropped into a cooled liquid mixture of sulfuric acid (2.35 g, 24 mmol) and water (300 ml). At this time, the inside temperature was 3 to 5° C. The resulting mixture was separated into two layers. The aqueous layer was extracted with diisopropyl ether (200 ml two times). All the extracted organic layers were combined into one and concentrated by a rotary evaporator. The concentration residue was treated by column chromatography. As a result, the target fluorine-containing cyclopropane diester of the following formula was obtained in an amount of 25.68 g. The content of the target diester was 85.83 mmol. The yield of the target diester was 72%.

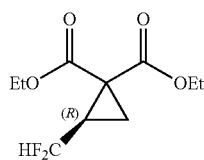

Example 12

Provided was a 200-ml four-neck flask with a thermometer well, a Dimroth condenser, a septum and a mechanical stirrer. After the inside of the flask was replaced by nitrogen, THF (50 ml), n-heptane (10 ml) and sodium hydride (2.17 g, 54.2 mmol) were put into the flask. The flask was heated in an oil bath of 80° C. until the inside temperature of the flask became 68° C. While the inside of the flask was maintained at this temperature, a mixture of diethyl malonate (4.34 g, 27.1 mmol) and a fluorine-containing cyclic sulfate of the following formula (chemical purity: 94.3 wt %, 5.00 g, 27.1 mmol) was gradually dropped into the flask over 5 hours.

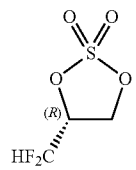

After the completion of the dropping, the contents of the flask were stirred for 1.5 hours while the inside temperature of the flask was maintained at 68° C. The flask was then returned to room temperature. Subsequently, 58 g of methyl tert-butyl ether was added into the flask. The thus-obtained reaction solution was dropped into 29 g of a 1 wt % aqueous sulfuric acid. The resulting mixture was separated into two layers. The organic layer was analyzed by $^{19}$F-NMR. It was found that the target fluorine-containing cyclopropane diester of the following formula was obtained in an amount of 85.83 mmol (4.72 g). The yield of the target diester was 74%.

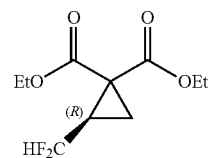

Example 13

Provided was a 200-ml four-neck flask with a thermometer well, a Dimroth condenser, a septum and a mechanical stirrer. After the inside of the flask was replaced by nitrogen, THF (45 ml) and diethyl malonate (3.31 g, 20.7 mmol) were put into the flask. The flask was cooled by ice water. Next, sodium metal (0.58 g, 25.3 mmol) was put into the flask. The contents of the flask were stirred for 2 hours while the inside temperature of the flask was set to 6 to 9° C. The contents of the flask were further stirred for 2 hours at room temperature. The flask was cooled by ice water. Subsequently, a mixture of a fluorine-containing cyclic sulfate of the following formula (chemical purity: 86 wt %, optical purity: 78.2% ee, 3.01 g, 14.9 mmol), THF (7 ml) and benzotrifluoride (1.49 g, 10.2 mmol) as an internal standard material was gradually dropped into the flask over 10 minutes.

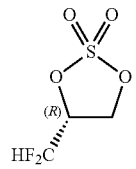

At this time, the inside temperature of the flask was about 6° C. After the completion of the dropping, the contents of the flask were stirred for 1 hour while the flask was cooled by ice water. Then, the inside temperature of the flask was raised to room temperature. Into the flask, sodium metal (0.47 g, 20.3 mmol) was added. The contents of the flask were stirred for 20 minutes at room temperature. The contents of the flask were further stirred for 1.5 hours while the flask was heated in an oil bath to an inside temperature of about 67° C. The thus-obtained reaction solution was cooled to room temperature and left still overnight at room temperature. After left still, the reaction solution was analyzed. It was found that the target fluorine-containing cyclopropane diester of the following formula was obtained. The content of the target diester was 12.1 mmol. The yield of the target diester was 81%.

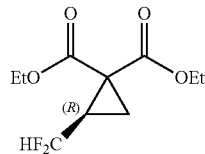

Further, the reaction solution was gradually dropped into a cooled liquid mixture of sulfuric acid (0.76 g, 7.8 mmol) and water (57 ml). The resulting mixture was separated into two layers. The aqueous layer was extracted with diisopropyl ether (30 ml three times). All the extracted organic layers were combined into one and concentrated by a rotary evaporator. As a result of the concentration, the target fluorine-containing cyclopropane diester was obtained in an amount of 4.0 g. The content of the target diester was 6.71 mmol. The yield of the target diester was 45%.

Example 14

Into a 300-ml three-neck flask with a thermometer well and a cock, the fluorine-containing cyclopropane diester of the following formula (purity: 90 wt %, 4.5 g, 17.1 mmol) obtained in Example 6, ethanol (8.6 ml) and water (8.6 ml) were put. The flask was cooled by ice water.

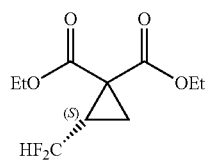

Next, a 25% aqueous solution of tetramethylammonium hydroxide (9.4 g, 25.7 mmol) was gradually dropped into the flask. At this time, the inside temperature of the flask was 2 to 5° C. After the completion of the dropping, the thus-obtained reaction solution was stirred for 30 minutes while the flask was kept cooled by ice water. Subsequently, the temperature of the reaction solution was raised to about 15° C. To the reaction solution, 50 ml of ethyl acetate and 10 ml of a 3 M aqueous hydrochloric acid solution were added.

The resulting mixture was mixed and separated into two layers. The aqueous layer was extracted with ethyl acetate (20 ml×3). The extracted organic layers were combined into one and washed with 10 ml of water. The washed organic layer was dehydrated with sodium sulfate, and then, subjected to filtration. The filtrate was concentrated by a rotary evaporator. As a result, a crude product of the target fluorine-containing cyclopropane monoester of the following formula was obtained in an amount of 3.4 g.

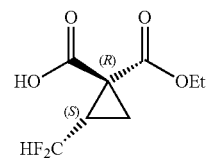

The diastereomer excess of the crude product was 56% de. The total diastereomer content of the crude product was 13.7 mmol. The NMR data of the target monoester was as follows: $^1$H-NMR (deuterated solvent: deuterated methanol, reference material: tetramethylsilane) δ ppm: 1.27 (t, 3H), 1.70 (ddd, 1H), 1.52 (ddd, 1H), 2.29 (m, 1H), 4.21 (q, 2H), 5.77 (td, 1H); $^{19}$F-NMR (deuterated solvent: deuterated methanol, reference material: hexafluorobenzene set as −162.2 ppm) −115.4 (ddd, 1F), −110.0 (ddd, 1F).

Example 15

Into a 20-ml two-neck flask with a thermometer well and a cock, 1.47 g (5.67 mmol) of the fluorine-containing cyclopropane monoester of the following formula obtained in Example 14, 1.5 ml of isopropanol and (S)-1-phenylethylamine (0.76 g, 6.23 mmol) were put. The flask was heated in an oil bath of 50° C.

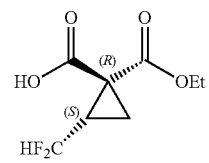

Next, 9 ml of n-heptane was dropped into the flask. While the contents of the flask were stirred, the flask was gradually cooled to room temperature. When the inside temperature of the flask was lowered to room temperature, a precipitated crystal was filtered out. The filtered crystal was dried by a rotary evaporator until there occurred no change in the weight of the crystal. As a result, the target amine salt was obtained in an amount of 1.04 g. To 0.9 g of the obtained crystal, 0.9 ml of isopropanol was added. The resulting mixture was heated by an oil bath of 50° C. Further, 5.4 ml of n-heptane was added to the mixture. The mixture was left under room temperature and thereby gradually cooled to about room temperature while stirring. After that, the mixture was cooled by ice water and subjected to filtration. The thus-obtained crystal was dried by a rotary evaporator until there occurred no change in the weight of the crystal. As a result, the target compound of the following formula was obtained in an amount of 0.38 g.

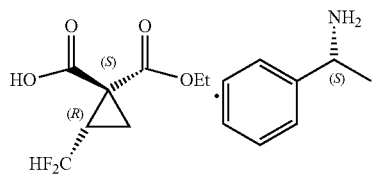

The NMR data of the target compound was as follows: $^1$H-NMR (deuterated solvent: deuterated methanol, reference material: tetramethylsilane) δ ppm: 1.25 (t, 3H), 1.31

(ddd, 1H), 1.42 (ddd, 1H), 1.62 (d, 3H), 2.13 (m, 1H), 4.17 (m, 2H), 4.44 (q, 1H), 5.66 (td, 1H), 7.36-7.49 (m, 5H); $^{19}$F-NMR (deuterated solvent: deuterated methanol, reference material: hexafluorobenzene set as −162.2 ppm) −114.7 (ddd, 1F), −108.6 (ddd, 1F). The diastereomer excess of the target compound was 99% de.

Example 16

Measurement of Optical Purity:

With the crystal (100 mg, 0.304 mmol) obtained in Example 15, a 3 M aqueous HCl solution (5 ml, 13.9 mmol) and methyl tert-butyl ether (10 ml) were added and mixed. The mixture was mixed until complete dissolution of the crystal. Then, the mixture was separated into two layers. To the organic layer, sulfuric acid (0.1 g, 1.0 mmol), triethyl orthoformate (3.4 g, 22.7 mmol) and ethanol (15 ml) were added. The thus-obtained solution was reacted by stirring for 12 hours at 70° C. After the reaction, the solution was concentrated. To the concentration residue, 1 ml of water and 5 ml of methyl tert-butyl ether were added. The resulting liquid mixture was isolated and separated into two layers. The organic layer was again concentrated. This concentration residue was analyzed by HPLC. The optical purity of the target compound was 99.1% ee. The HPLC analysis conditions were as follows: column: CHIRALCEL OZ-3, eluent: n-heptane/isopropanol=99.5/0.5, flow rate: 1 ml/min, detector: UV 210 nm, column temperature: 25° C., retention time: (S)-isomer: 8.4 min., (R)-isomer: 9.6 min.

Example 17

Into a 300-ml two-neck flask with a thermometer well and a cock, the cyclopropane diester of the following formula (purity: 73.6 wt %, 9.7 g, 30.3 mmol) obtained in Example 10, ethanol (15 ml) and water (15 ml) were put. The flask was cooled to an inside temperature of about 2° C.

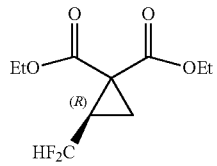

Next, a 25% aqueous solution of tetramethylammonium hydroxide (16.6 g, 45.5 mmol) was gradually dropped into the flask. At this time, the inside temperature of the flask was 2 to 15° C. After the completion of the dropping, the contents of the flask were stirred for 30 minutes while the flask was cooled by ice water. The temperature of the thus-obtained reaction solution was raised to about 15° C. To the reaction solution, 100 ml of ethyl acetate and 20 ml of a 3 M aqueous hydrochloric acid solution were added. The resulting mixture was mixed and separated into two layers. The aqueous layer was extracted with ethyl acetate (40 ml×3). The extracted organic layers were combined into one and washed with 20 ml of water. The washed organic layer was dehydrated with sodium sulfate and subjected to filtration. To the filtrate, 0.6 g of activated carbon was added. Then, the filtrate was stirred for 1 hour at room temperature and subjected to filtration. The filtrate solution was concentrated by a rotary evaporator. As a result, a crude product of the target compound of the following formula was obtained in an amount of 8.6 g.

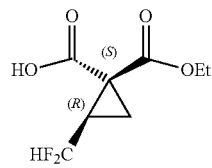

The diastereomer excess of the target compound was 56% de. The total yield of diastereomers of the target compound was almost quantitative. The NMR data of the target compound was as follows: $^1$H-NMR (deuterated solvent: deuterated methanol, reference material: tetramethylsilane) δ ppm: 1.27 (t, 3H), 1.70 (ddd, 1H), 1.52 (ddd, 1H), 2.29 (m, 1H), 4.21 (q, 2H), 5.77 (td, 1H); $^{19}$F-NMR (deuterated solvent: deuterated methanol, reference material: hexafluorobenzene set as −162.2 ppm) −115.4 (ddd, 1F), −110.0 (ddd, 1F).

Example 18

Into a 300-ml three-neck flask with a thermometer well and a cock, (R)-fluorine-containing cyclopropane diester of the following formula (purity: 78.5 wt %, 5.58 g, 18.5 mmol), ethanol (9.2 ml) and water (9.2 ml) were put. The flask was cooled to an inside temperature of about 4 to 5° C.

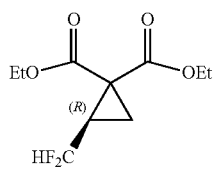

Next, a 40% aqueous solution of sodium hydroxide (3.5 g, 35.2 mmol) was gradually dropped into the flask. At this time, the inside temperature of the flask was 4 to 8° C. While the flask was cooled by ice water, the contents of the flask were stirred for 1 hour. To the thus-obtained reaction solution, 50 ml of ethyl acetate and 10 ml of a 3 M aqueous hydrochloric acid solution were added. The resulting mixture was mixed and separated into two layers. The aqueous layer was extracted with ethyl acetate (20 ml×3). All the extracted organic layers were combined into one and washed with 20 ml of water. The washed organic layer was dehydrated with sodium sulfate and subjected to filtration. To the filtrate, 0.2 g of activated carbon was added. Then, the filtrate was stirred for 30 minutes at room temperature and subjected to filtration. The filtrate solution was concentrated by a rotary evaporator. The concentration residue was subjected to azeotropic dehydration with the addition of toluene. Finally, all the organic solvent was removed. As a result, a crude product of the target compound of the following formula was obtained in an amount of 4.68 g.

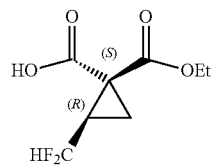

The diastereomer excess of the crude product was 72% de. The total diastereomer content of the crude product was 13.6 mmol.

Example 19

In a 100-ml three-neck flask with a thermometer well and a cock, 8.6 g of the fluorine-containing cyclopropane monoester of the following formula obtained in Example 17, 8.6 ml of isopropanol and 43 ml of n-heptane were put.

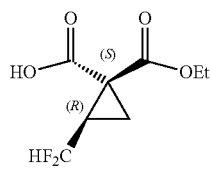

This solution was cooled by ice water, followed by adding thereto (R)-1-phenylethylamine (4.4 g, 34.6 mmol). The solution was stirred for 30 minutes at around room temperature, and then, heated by an oil bath to an inside temperature of about 67° C. while stirring by a stirrer. After confirming that the solution became uniform by the heating and stirring, the oil bath was removed. The solution was cooled under room temperature while stirring. At the time when the temperature of the solution became 53° C., 10 mg of a seed crystal was added into the solution. The precipitation of a crystal was started when the temperature of the solution became 40 to 50° C. When the temperature of the reaction solution became 28° C., the solution was cooled by ice water to 0 to 5° C. After that, the solution was subjected to filtration. The filtered crystal was washed with 26 ml of a 1:10 mixed liquid of isopropanol and n-heptane. The washed crystal was dried by a rotary evaporator until there occurred no change in the weight of the crystal. Then, the target fluorine-containing cyclopropane monoester salt was obtained in an amount of 6.37 g. To 6.27 g of the obtained crystal, 6.3 ml of isopropanol was added. The resulting mixture was heated to about 70° C. by an oil bath while stirring by a stirrer. It was confirmed that the mixture became a uniform solution by dissolution of the crystal. When 19 ml of n-heptane was added to the solution, a crystal precipitate was formed. After 19 ml of n-heptane was added to the solution, the cooling of the solution was started upon removal of the oil bath. At the time when the temperature of the solution became about 43° C., 13 ml of n-heptane was added to the solution. When the temperature of the solution became 28° C., the solution was cooled by ice water to 0 to 5° C. The precipitated crystal was filtered out. The filtered crystal was dried by a rotary evaporator until there occurred no change in the weight of the crystal. As a result, the target compound of the following formula was obtained in an amount of 5.66 g.

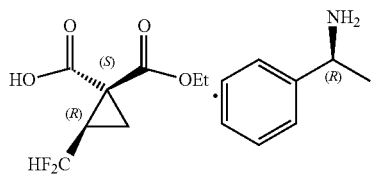

The NMR data of the target compound was as follows: $^1$H-NMR (deuterated solvent: deuterated methanol, reference material: tetramethylsilane) δ ppm: 1.25 (t, 3H), 1.31 (ddd, 1H), 1.41 (ddd, 1H), 1.62 (d, 3H), 2.12 (m, 1H), 4.15 (q, 2H), 4.44 (q, 1H), 5.66 (td, 1H), 7.37-7.47 (m, 5H); $^{19}$F-NMR (deuterated solvent: deuterated methanol, reference material: hexafluorobenzene set as −162.2 ppm) −114.6 (ddd, 1F), −108.7 (ddd, 1F). The diastereomer excess of the target compound was 99% de. The optical purity of the target compound was 99.3% ee as measured by reference to Example 16.

Example 20

In a 300-ml two-neck flask with a thermometer well and a cock, the fluorine-containing cyclopropane diester of the following formula (as a racemic mixture, purity: 58.8 wt %, 8.85 g, 22.0 mmol) obtained in Example 2, ethanol (11 ml) and water (11 ml) were put. The flask was cooled to an inside temperature of about 2° C.

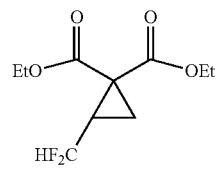

Next, a 25% aqueous solution of tetramethylammonium hydroxide (17.1 g, 26.4 mmol) was gradually dropped into the flask. At this time, the inside temperature of the flask was 2 to 10° C. While the flask was cooled by ice water, the contents of the flask were stirred for 1 hour. To the thus-obtained reaction solution, 50 ml of ethyl acetate and 10 ml of a 3 M aqueous hydrochloric acid solution were added. The resulting mixture was mixed and separated into two layers. The aqueous layer was extracted with ethyl acetate (20 ml×3). All the extracted organic layers were combined into one and washed with 20 ml of water. The washed organic layer was dehydrated with sodium sulfate and subjected to filtration. To the filtrate, 0.2 g of activated carbon was added. Then, the filtrate was stirred for 2 hours at room temperature and subjected to filtration. The filtrate solution was concentrated by a rotary evaporator. As a result, a crude product of the target compound of the following formula was obtained in an amount of 6.35 g.

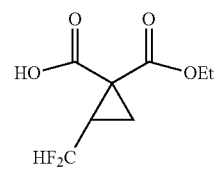

The diastereomer excess of the target compound was 86% de. The total yield of diastereomers of the target compound was almost quantitative. The NMR data of the target compound was as follows: $^1$H-NMR (deuterated solvent: deuterated methanol, reference material: tetramethylsilane) δ ppm: 1.27 (t, 3H), 1.70 (ddd, 1H), 1.52 (ddd, 1H), 2.29 (m, 1H), 4.21 (q, 2H), 5.77 (td, 1H); $^{19}$F-NMR (deuterated solvent: deuterated methanol, reference material: hexafluorobenzene set as −162.2 ppm) −115.4 (ddd, 1F), −110.0 (ddd, 1F).

Example 21

Into a 100-ml three-neck flask with a Dimroth condenser, a thermometer well and a cock, 6.35 g of the fluorine-containing cyclopropane monoester of the following formula obtained in Example 20, 6.4 ml of diisopropyl ether and 12.8 ml of n-hexane were put.

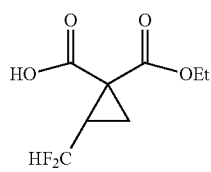

To this solution, (R)-1-phenylethylamine (3.26 g, 26.9 mmol) was added. The flask was heated in an oil path to an inside temperature of about 69° C. After that, the flask was taken out of the oil bath. The solution was then cooled under room temperature while stirring. At the time when the inside temperature of the flask became about 69° C., about 20 mg of a crystal of a compound of the following formula was added as a seed crystal to the solution.

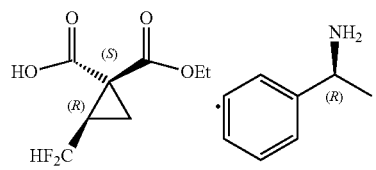

At the time when the inside temperature of the flask became about 35° C., about 20 mg of the seed crystal was further added to the solution. When the temperature of the solution was lowered to about room temperature, the flask was cooled by ice water. At the time when the temperature of the solution became about 8° C., about 20 mg of the seed crystal was further added to the solution. After that, the solution was stirred overnight while the flask was placed in a constant low-temperature bath with a magnetic stirrer (PSL Series available from TOKYO RIKAKIKI CO., LTD.). Herein, the temperature of the constant low-temperature bath was set to 0° C. When the solution was cooled to 0 to 5° C., a crystal was precipitated. The precipitated crystal was filtered out and dried by a rotary evaporator until there occurred no change in the weight of the crystal. To the obtained crystal, 12.8 ml of diisopropyl ether was added. The resulting mixture was heated to about 67° C. by an oil bath. After confirming dissolution of the crystal, the oil bath was removed. The thus-obtained solution was gradually cooled under room temperature. At the time when the temperature of the solution became about 67° C., about 10 mg of the seed crystal was added to the solution. After that, about 10 mg of the seed crystal was further added to the solution at the time when the temperature of the solution became about 20° C. The solution was stirred for some time. Then, a crystal precipitate was formed. The solution was further cooled by ice water and then subjected to filtration. The filtered crystal was dried by a rotary evaporator until there occurred no change in the weight of the crystal. As a result, the target compound of the following formula was obtained in an amount of 0.99 g. The yield of the target compound was 19%.

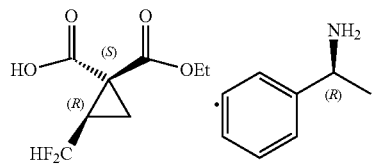

The diastereomer excess of the target compound was 96.9% de. The optical purity of the target compound was 25.6% ee as measured by reference to Example 16.

Example 22

Into a 500-ml three-neck flask with a thermometer well and a cock, (R)-fluorine-containing cyclopropane diester of the following formula (purity: 63.2 wt %, 128.5 g, 343.8 mmol) and ethanol (69 ml) were put. The flask was cooled to an inside temperature of −5° C.

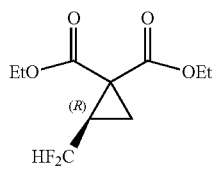

Next, a 48% aqueous solution of 2-hydroxyethyltrimethylammonium hydroxide (130.2 g, 515.7 mmol) was gradually added into the flask. At this time, the inside temperature of the flask was −5 to −2° C. The contents of the flask were stirred for 8 hours while the inside temperature of the flask was maintained at −2° C. To the thus-obtained reaction solution, 258 g of methyl tert-butyl ether and 261 g of a 3.2 M aqueous hydrochloric acid solution were added. The resulting mixture was separated into two layers. The aqueous layer was extracted with methyl tert-butyl ether (103 g×2). All the extracted organic layers were combined into one and washed with 138 ml of water. The washed organic layer was concentrated by a rotary evaporator. The concentration residue was subjected to azeotropic dehydration with the addition of toluene (120 g×2). Finally, all the organic solvent was removed. As a result, a crude product of the target compound of the following formula was obtained in an amount of 100.3 g. The diastereomer excess of the crude product was 65.3% de.

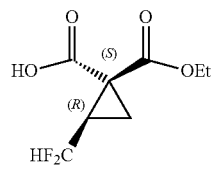

Example 23

Into a 500-ml three-neck flask with a thermometer well and a cock, 50.2 g of the fluorine-containing cyclopropane monoester of the following formula obtained in Example 22, 27 g of isopropanol and 133 g of methylcyclohexane were put.

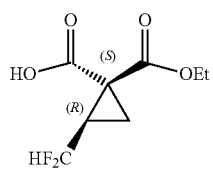

This solution was cooled by ice water, followed by adding thereto (R)-1-phenylethylamine (22.0 g, 181.5 mmol). The solution was heated by an oil bath to about 70° C. while stirring. After confirming that the solution became uniform by the heating and stirring, the oil bath was removed. The solution was cooled under room temperature while stirring. The solution was further stirred for 1 hour after the inside temperature of the flask became 20° C. The solution was subjected to filtration so as to recover a precipitated crystal. The filtered crystal was washed with a mixed liquid of 5 g of isopropanol and 27 g of methylcyclohexane. The washed crystal was dried by a rotary evaporator until there occurred no change in the weight of the crystal. Then, the target fluorine-containing cyclopropane monoester salt was obtained in an amount of 36.7 g. The yield of the target monoester salt was 65%. To the whole of the obtained crystal, 27 g of isopropanol and 132 g of cyclomethylhexane were added. The resulting mixture was heated to about 70° C. by an oil bath while stirring. After confirming that the mixture became a uniform solution by dissolution of the crystal, the oil bath was removed. The solution was cooled while stirring. When the temperature of the solution became about 44° C., a crystal was precipitated. The solution was further stirred for 1 hour at 20° C. and then subjected to filtration. The filtered crystal was dried by a rotary evaporator until there occurred no change in the weight of the crystal. As a result, the target compound of the following formula was obtained in an amount of 29.5 g. The yield of the target compound was 51%.

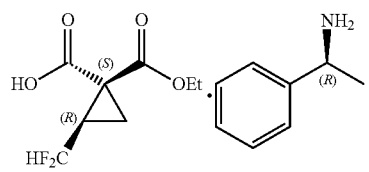

The diastereomer excess of the target compound was 99% de. The optical purity of the target compound was 99.7% ee as measured by reference to Example 16.

Example 24

Into a 500-ml three-neck flask with a thermometer well and a cock, 25.1 g of the fluorine-containing cyclopropane monoester of the following formula obtained in Example 22 and 31 ml of diisopropyl ether were put. This solution was cooled by ice water, followed by adding thereto (S)-1-phenylethylamine (10.9 g, 90.3 mmol).

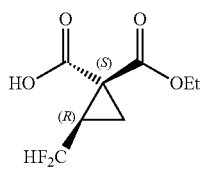

The solution was heated by an oil bath to 65° C. while stirring. After confirming that the solution became uniform by the heating and stirring, the oil bath was removed. The solution was cooled under room temperature while stirring. The solution was further stirred for 1 hour after the inside temperature of the flask became 20° C. Then, the solution was subjected to filtration. As a result, the target fluorine-containing cyclopropane monoester salt of the following formula was obtained in an amount of 15.1 g. The yield of the target compound was 53%.

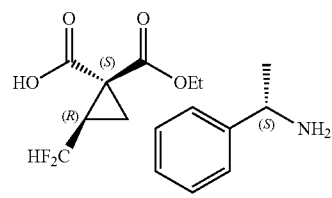

The diastereomer excess of the target compound was 95.0% de. The optical purity of the target compound was 93.2% ee as measured by reference to Example 16. The NMR data of the target compound was as follows: $^1$H-NMR (deuterated solvent: deuterated methanol, reference material: tetramethylsilane) δ ppm: 1.23 (t, 3H), 1.30 (ddd, 1H), 1.40 (ddd, 1H), 1.61 (d, 3H), 2.11 (m, 1H), 4.15 (m, 2H), 4.42 (q, 1H), 5.66 (td, 1H), 7.30-7.46 (m, 5H); $^{19}$F-NMR (deuterated solvent: deuterated methanol, reference material: hexafluorobenzene set as −162.2 ppm) −114.7 (ddd, 1F), −108.6 (ddd, 1F).

Example 25

Into a three-neck flask with a thermometer well and a cock, (R)-fluorine-containing cyclopropane diester of the following formula (purity: 73.8 wt %, 3.2 g, 10.0 mmol) and ethanol (2 ml) were put. The flask was cooled to an inside temperature of −5° C.

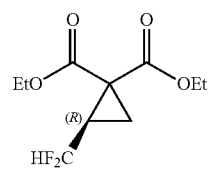

Next, a 48% aqueous solution of 2-hyroxyethyltrimethylammonium hydroxide (5.1 g, 20.0 mmol) was gradually added into the flask. At this time, the inside temperature of the flask was −8 to −10° C. The contents of the flask were stirred for 4 hours while the inside temperature of the flask was maintained at −4° C. To the thus-obtained reaction solution, 7.5 g of methyl tert-butyl ether and 7.5 g of a 3.2 M aqueous hydrochloric acid solution were added. The resulting mixture was mixed and separated into two layers. The aqueous layer was extracted with methyl tert-butyl ether (3.0 g×2). All the extracted organic layers were combined into one and washed with 4.0 ml of water. The washed organic layer was concentrated by a rotary evaporator. The concentration residue was subjected to azeotropic dehydration with the addition of toluene (3.5 g×2). To the obtained crude product, 1.6 g of isopropanol and 7.7 g of methylcyclohexane were added. The resulting solution was cooled by ice water, followed by adding thereto (R)-1-(1-naphthyl)

ethylamine (1.8 g, 10.5 mmol). The solution was heated to 70° C. by an oil bath while stirring. After confirming that the solution became uniform by the heating and stirring, the oil bath was removed. The solution was cooled under room temperature while stirring. The solution was further stirred for 1 hour after the temperature of the solution became 3° C. Then, the solution was subjected to filtration so as to recover a precipitated crystal. The filtered crystal was washed with a mixed liquid of 0.3 g of isopropanol and 1.5 g of methylcyclohexane. To the whole of the washed crystal, 1.6 g of isopropanol and 7.7 g of cyclomethylhexane were added. The resulting mixture was heated to 70° C. by an oil bath while stirring. After confirming that the mixture became a uniform solution by dissolution of the crystal, the oil bath was removed. The solution was cooled while stirring. The solution was further stirred for 1 hour at −5° C. and then subjected to filtration so as to recover a precipitated crystal. The filtered crystal was dried by a rotary evaporator until there occurred no change in the weight of the crystal. As a result, the target fluorine-containing cyclopropane monoester salt of the following formula was obtained in an amount of 0.61 g. The yield of the target monoester salt was 16%.

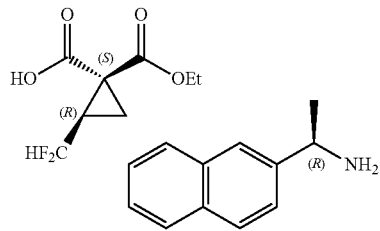

The NMR data of the target monoester salt was as follows: $^1$H-NMR (deuterated solvent: deuterated methanol, reference material: tetramethylsilane) δ ppm: 1.25 (t, 3H), 1.32 (m, 1H), 1.42 (dd, 1H), 1.75 (d, 3H), 2.14 (m, 1H), 4.18 (m, 2H), 5.38 (q, 1H), 5.67 (td, 1H), 7.62 (m, 4H), 7.96 (t, 2H), 8.15 (d, 1H); $^{19}$F-NMR (deuterated solvent: deuterated methanol, reference material: hexafluorobenzene set as −162.2 ppm) −117.0 (ddd, 1F), −111.0 (ddd, 1F). The diastereomer excess of the target compound was 98.6% de. The optical purity of the target compound was 92.3% ee as measured by reference to Example 16.

Example 26

Provided was a 300-ml four-neck flask with a thermometer well, a Dimroth condenser, a septum and a mechanical stirrer. After the inside of the flask was replaced by nitrogen, THF (131 ml), n-heptane (26 ml) and 60 wt % sodium hydride (7.5 g, 188 mmol) were put into the flask. The flask heated in an oil bath of 80° C. until the inside temperature of the flask became 66° C. While the inside of the flask was maintained at this temperature, a mixture of dimethyl malonate (12.4 g, 93.9 mmol) and a fluorine-containing cyclic sulfate of the following formula (chemical purity: 94.6 wt %, 17.3 g, 93.9 mmol) was dropped into the flask over 5 hours.

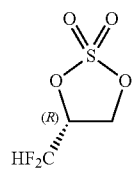

After the completion of the dropping, the contents of the flask were stirred for 3 hours while the inside temperature of the flask was maintained at 66° C. The inside of the flask was then returned to room temperature. Acetic acid (5.6 g) was added into the flask. After that, 140 ml of methyl tert-butyl ether was added into the flask. The thus-obtained solution was separated into two layers. The organic layer was concentrated, and then, analyzed by $^{19}$F-NMR. It was found by the analysis that the target fluorine-containing cyclopropane diester of the following formula was obtained with a crude weight of 9.5 g. The content of the target diester was 6.3 g, 30.5 mmol. The yield of the target diester was 32%.

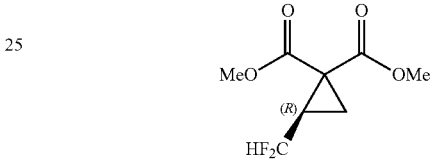

The NMR data of the target diester was as follows: $^1$H-NMR (deuterated solvent: deuterated chloroform, reference material: tetramethylsilane) δ ppm: 1.58 (m, 1H), 1.78 (m, 1H), 2.37 (m, 1H), 3.77 (s, 3H), 3.79 (s, 3H), 5.74 (td, 1H); $^{19}$F-NMR (deuterated solvent: deuterated chloroform, reference material: hexafluorobenzene set as −162.2 ppm) −118.0 (ddd, 1F), −112.0 (ddd, 1F).

Example 27

Into a three-neck flask with a thermometer well and a cock, a (R)-fluorine-containing cyclopropane diester of the following formula (purity: 66.6 wt %, 9.5 g as a content of 6.3 g, 30.5 mmol) obtained in Example 26 and methanol (6 ml) were put. The flask was cooled to an inside temperature of −8° C.

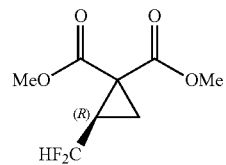

Next, a 48% aqueous solution of 2-hydroxyethyltrimethylammonium hydroxide (11.5 g, 45.7 mmol) was gradually added into the flask. At this time, the inside temperature of the flask was −8 to −1° C. While the inside of the flask was maintained at this temperature, the contents of the flask was stirred for 2 hours. To the thus-obtained reaction solution, 30 g of methyl tert-butyl ether and 22.3 g of a 2.8 M aqueous hydrochloric acid solution were added. The resulting mixture was mixed and separated into two layers. The aqueous layer was extracted with methyl tert-butyl ether (15 g×2). All of the extracted organic layers were combined into one and washed with 12 ml of water. The washed organic layer was concentrated by a rotatory evaporator. The concentration residue was subjected to azeotropic dehydration with the addition of toluene (15 g×2). Finally, all the organic solvent was removed. As a result, a crude product of the target compound of the following formula was obtained in an amount of 8.84 g.

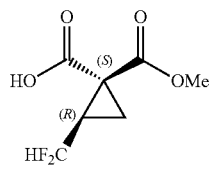

To the whole of the crude product, 10.6 ml of isopropanol and 30.5 ml of methylcyclohexane were added. Subsequently, (R)-1-phenylethylamine (4.1 g, 33.5 mmol) was added to the crude product solution. The solution was heated by an oil bath to 74° C. while stirring. After confirming that the solution became uniform by the heating and stirring, the oil bath was removed. The solution was cooled under room temperature while stirring. The solution was further stirred for 1 hour after the temperature of the solution became 26° C. The solution was subjected to filtration so as to recover a precipitated crystal. The filtered crystal was dried by a rotary evaporator until there occurred no change in the weight of the crystal. Then, the target fluorine-containing cyclopropane monoester salt was obtained in an amount of 6.5 g. To the whole of the obtained crystal, 11.6 ml of isopropanol and 30.5 ml of methylcyclohexane were added. The resulting mixture was heated to 75° C. by an oil bath while stirring. After confirming that the mixture became a uniform solution by dissolution of the crystal, the oil bath was removed. The solution was cooled while stirring. When the temperature of the solution became about 60° C., a crystal was precipitated. The solution was further stirred for 1 hour at 24° C. and then subjected to filtration. The filtered crystal was dried by a rotary evaporator until there occurred no change in the weight of the crystal. As a result, the target compound of the following formula was obtained in an amount of 4.7 g. The yield of the target compound was 49%.

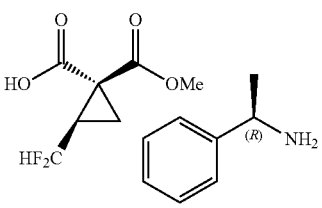

The diastereomer excess of the target compound was 83% de. The target compound was subjected to methyl esterification with the addition of trimethyl orthoformate and methanol according to the method used in Example 16. The optical purity of this compound was 99% ee as measured by reference to Example 16. The NMR data of the target compound was as follows: $^1$H-NMR (deuterated solvent: deuterated methanol, reference material: tetramethylsilane) δ ppm: 1.31 (m, 1H), 1.42 (m, 1H), 1.62 (d, 3H), 2.11 (m, 1H), 3.70 (s, 3H), 4.43 (q, 1H), 5.65 (td, 1H), 7.42 (m, 5H); $^{19}$F-NMR (deuterated solvent: deuterated methanol, reference material: hexafluorobenzene set as −162.2 ppm) −114.9 (ddd, 1F), −108.9 (ddd, 1F).

Reference Example 1

By reference to International Publication No. WO 2014/078220, 3,3-difluorolactic acid amide was formed. To 190 ml (1.2 mL/mmol) of water, 20 g (160 mmol, 1.0 eq) of the 3,3-difluorolactic acid amide and 78 g (800 mmol, 5.0 eq) of sulfuric acid were added. The resulting solution was reacted by stirring for 20 hours at 100° C. After the completion of the reaction, the solution was extracted with 2-methyltetrahydrofuran. The recovered organic layer was concentrated under vacuum, thereby obtaining 16 g (130 mmol) of 3,3-difluorolactic acid. The yield of the 3,3-difluorolactic acid was 81%. To 5.5 g (120 mmol, 1.5 eq) of ethanol, 10 g (79 mmol, 1.0 eq) of the 3,3-difluorolactic acid, 17.8 g (120 mmol, 1.5 eq) of triethyl orthoformate and 1.2 g (12 mmol, 0.15 eq) of sulfuric acid were added. The resulting solution was reacted by stirring overnight at room temperature. After the completion of the reaction, the solution was subjected to simple distillation (jacket temperature: 50 to 110° C., vacuum degree: 5 to 50 torr). As a result, ethyl 3,3-difluorolactate was obtained in an amount of 10.6 g (69 mmol). The yield of the ethyl 3,3-difluorolactate was 87%. The NMR data of the ethyl 3,3-difluorolactate was as follows: $^1$H-NMR (reference material: tetramethylsilane, deuterated solvent: deuterated chloroform) δ ppm: 1.34 (t, 3H), 4.29-4.43 (m, 3H), 5.97 (dt, 1H); proton of hydroxy group was unidentified; $^{19}$F-NMR (reference material: hexafluorobenzene set as −162.2 ppm, deuterated solvent: deuterated chloroform) δ ppm: −131.0 (ddd, 1F), −129.6 (ddd, 1F).

Reference Example 2

Into a 5-L four-neck flask with a Dimroth condenser, a thermometer well, a cock and a mechanical stirrer, 606 g (3.93 mol) of ethyl 3,3-difluorolactate and 3.6 L of ethanol were put. The flask was cooled to an inside temperature of about 10° C. Next, 223 g (5.90 mol) of sodium borohydride was gradually dropped into the flask over 4 hours. At the time, the inside temperature of the flask was 10 to 30° C. After the completion of the dropping, the contents of the flask were stirred for 2 hours while the inside temperature of the flask was set to 20 to 30° C. The contents of the flask were further stirred overnight at room temperature. The thus-obtained reaction solution was analyzed by gas chromatography. The disappearance of the raw material was confirmed by the analysis. Subsequently, the reaction solution was concentrated by a rotary evaporator until the weight of the concentration residue became 1681 g. To the concentration residue, 1515 ml of a 4 N aqueous HCl solution was added. At this time, the temperature was raised to 58° C. by heat generation. After that, the resulting solution was stirred overnight at room temperature. The stirred solution was cooled by ice water and subjected to filtration so as to remove a precipitate. The filtrate was analyzed by $^{19}$F-NMR. It was found that the target 1,1-difluoro-2,3-propanediol was formed almost quantitatively. The filtrate was concentrated by a rotary evaporator. The concentration was once stopped at the time when the weight of the concentration residue became 2050 g. The concentrate was then subjected to filtration. The filtered substance was washed with 600 ml of toluene. The filtrate and the washing liquid were combined into one and concentrated by a rotary evaporator. The concentration was stopped at the time when the weight of the concentration residue became 673.5 g. The concentrate was again subjected to filtration. The filtered substrate was washed with 100 ml of toluene. The filtrate and the washing liquid were combined into one and concentrated by a rotary evaporator. When the weight of the concentration residue became 515.6 g, the concentrate was subjected to flash distillation by a distillation unit under conditions of a jacket temperature of 60 to 120° C. and a pressure of 0.001 MPa. As a result, the target 3,3-difluoro-1,2-propanediol of the following formula was obtained in an amount of 394.9 g. The purity of the target compound was 83.7 wt %. The content of the target compound was 3.002 mol. The yield of the target compound was 76.4%.

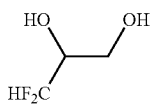

The NMR data of the target compound was as follows: $^1$H-NMR (deuterated solvent: deuterated acetonitrile, reference material: tetramethylsilane) δ ppm: 3.61 (m, 2H), 3.72 (m, 1H), 5.79 (td, 1H); proton of hydroxy group was unidentified; $^{19}$F-NMR (deuterated solvent: deuterated acetonitrile, reference material: hexafluorobenzene set as −162.2 ppm) −130.9 (ddd, 1F), −128.2 (ddd, 1F).

Reference Example 3

The 3,3-difluoro-1,2-propanediol obtained in Reference Example 2, which had a water content of 16.3 wt %, was dehydrated with the use of toluene. More specifically, azeotropic dehydration was performed by putting 30 g of the fraction obtained in Reference Example 2 and 100 ml of toluene into a 300-ml three-neck flask with a Dean-Stark apparatus, a thermometer well and a cock and setting the jacket temperature to 125 to 130° C. The dehydration was stopped when the azeotrope of water was no longer confirmed. The liquid mixture remaining in the flask was separated into two layers. Then, 21.9 g of 3,3-difluoro-1,2-propanediol was obtained. The yield of the 3,3-difluoro-1,2-propanediol was 87%. The water content of the 3,3-difluoro-1,2-propanediol was 0.47 wt % as measured with a Karl Fischer moisture meter.

Reference Example 4

As a medium for preculture, a culture fluid was prepared using 1000 ml of distilled water, 10 g of polypeptone, 5 g of yeast extract and 10 g of sodium chloride. The preculture fluid was aliquoted by 5 ml in each test tube (φ1.6 cm×15 cm) and subjected to steam sterilization for 15 minutes at 121° C. In this preculture fluid, genetically-modified Escherichia coli available from DAICEL CORPORATION as Chiralscreen (trademark) OH E039, which enable mass expression of alcohol dehydrogenase, was axenically inoculated by an inoculation loop and grown overnight at 30° C. and 160 spm. The thus-obtained preculture fluid had an optical density (OD600) of 8.2 at a wavelength of 600 nm. As a medium for culture, a culture fluid was prepared by mixing yeast extract, sodium glutamate, glucose, lactose, inorganic salt and antifoaming agent in 2500 ml of distilled water. The prepared culture fluid was introduced into a 5-L culture tank (MDN-type 5L(S) available from B.E. MARUBISHI CO., LTD.) and subjected to steam sterilization for 30 minutes at 121° C. In the culture tank, 5 ml of the preculture fluid was axenically inoculated and grown while stirring for 40 hours at a temperature of 30° C. and a ventilation rate of 0.5 vvm. As a result, there was obtained the culture fluid in suspension form having an optical density (OD600) of 24. During the culture, the pH of the culture fluid was adjusted to about 7.0 with the use of a 20% aqueous sodium carbonate solution and a 42.5% aqueous phosphoric acid solution. After the culture, the ventilation rate was changed to 0 vvm. Then, 3-chloro-1,1-difluoro-2-propanone hydrate was added in an amount of 6.25% wt/v (156.25 g), that is, 80% wt/wt relative to the culture fluid. In this culture fluid, the hydrate was subjected to reduction reaction for 24 hours at a pH of 6.2 while the coenzyme was regenerated by formate dehydrogenase. After the reaction, the rate of conversion to the target product compound was 96%; and the optical purity of the target product compound was 83.0% ee(R). The culture fluid after the reaction was subjected to vacuum distillation (inside pressure: 19.2 kPa, vapor temperature: 57 to 61° C.), thereby obtaining 443 g of an aqueous solution containing 80 g of (R)-1-chloro-3,3-difluoroisopropyl alcohol. The NMR data of the product compound was as follows: $^1$H-NMR (deuterated solvent: deuterated chloroform, reference material: tetramethylsilane) δ ppm: 3.72 (m, 2H), 4.03 (m, 1H), 5.86 (td, 1H); $^{19}$F-NMR (deuterated solvent: deuterated chloroform, reference material: hexafluorobenzene set as −162.2 ppm) −132.2 (ddd, 1F), −130.6 (ddd, 1F).

Reference Example 5

A part of the aqueous (R)-1-chloro-3,3-difluoroisopropyl alcohol solution obtained in Reference Example 4 was extracted such that the amount of the alcohol contained became 30 g. Then, 1.0 equivalent of a 48% aqueous sodium hydroxide solution was dropped into the extracted solution under cooling by ice water. The dropping was performed while monitoring and maintaining the temperature of the solution at 0 to 3° C. After the dropping, the resulting solution was subjected to ring-closing reaction by stirring for 120 minutes at 1° C. The solution was then subjected to distillation at a vapor temperature of 50 to 70° C. (atmospheric pressure), thereby obtaining 17 g of (S)-2-difluoromethylethylene oxide. The optical purity of this product compound was 83.1% ee as measured under the aftermentioned analysis conditions. The NMR data of the product compound was as follows: $^1$H-NMR (deuterated solvent: deuterated chloroform, reference material: tetramethylsilane) δ ppm: 2.8-2.9 (m, 2H), 3.27 (m, 1H), 5.56 (td, 1H); $^{19}$F-NMR (deuterated solvent: deuterated chloroform, reference material: hexafluorobenzene set as −162.2 ppm) −125.2 (ddd, 1F), −122.5 (ddd, 1F).

Reference Example 6

The 2-difluoromethylethylene oxide obtained in Reference Example 5 was converted to a sulfide compound by reaction with 1.1 equivalents of 2-naphthalenethiol and 1.1 equivalents of triethylamine. The sulfide compound was recovered as an analysis sample. The optical purity of this sample compound was determined from peak area measurements by high precision liquid chromatography under the following conditions: column: CHIRALCEL OD-H (4.6 mm×25 cm, particle size: 5 μm) available from DAICEL CORPORATION; mobile phase: n-hexane/IPA=95/5; flow rate: 0.7 ml; column temperature: 15° C.; and detection wavelength: 230 nm. The retention time of the R-enantiomer was 24.2 min; and the retention time of the S-enantiomer was 27.4 min.

Reference Example 7

To 17 g of the (S)-2-difluoromethylethylene oxide obtained in Reference Example 5, 0.2 equivalent of a 20% aqueous sulfuric acid solution was added. The resulting solution was reacted by stirring for 8 hours at 50° C. After the reaction, the pH of the solution was adjusted to 5 with the addition of sodium hydroxide. An inorganic salt was filtered out from the solution. The solution was then subjected to vacuum distillation (inside pressure: 1.5 kPa, vapor temperature: 80 to 81° C.), thereby obtaining 17 g of (S)-3,3-difluoro-1,2-propanediol. The optical purity of this product compound was 83.1% ee as measured under the after-mentioned analysis conditions. The NMR data of the product compound was as follows: $^1$H-NMR (deuterated solvent: deuterated acetonitrile, reference material: tetramethylsilane) δ ppm: 3.61 (m, 2H), 3.72 (m, 1H), 5.79 (td, 1H); $^{19}$F-NMR (deuterated solvent: deuterated acetonitrile, reference material: hexafluorobenzene set as −162.2 ppm) −130.9 (ddd, 1F), −128.2 (ddd, 1F).

Reference Example 8

The (S)-3,3-difluoro-1,2-propanediol obtained in Reference Example 7 was converted to a diacetoxy compound by reaction with 2.5 equivalents of acetic anhydride and 2.5 equivalents of pyridine. The diacetoxy compound was recovered as an analysis sample. The optical purity of this sample compound was determined from peak area measurements by gas chromatography under the following conditions: column: Cyclosil-B (0.25 mm×30 mm×0.25 μm) available from AGILENT TECHNOLOGIES, LTD.; carrier gas: nitrogen; pressure: 163 kPa; column temperature: 50° C. (5 min), 50 to 150° C. (5° C./min), 150° C. (15 min); and vaporization chamber/detector (FID) temperature: 230° C. The retention time of the R-enantiomer was 16.3 min; and the retention time of the S-enantiomer was 17.2 min. The configuration of the sample compound was determined based on known information.

Reference Example 9

As a medium for preculture, a culture fluid was prepared using 1000 ml of distilled water, 10 g of polypeptone, 5 g of yeast extract and 10 g of sodium chloride. The preculture fluid was aliquoted by 5 ml in each test tube (φ 1.6 cm×15 cm) and subjected to steam sterilization for 15 minutes at 121° C. In this preculture fluid, genetically-modified *Escherichia coli* available from DAICEL CORPORATION as Chiralscreen (trademark) OH E094, which enable mass expression of alcohol dehydrogenase, was axenically inoculated by an inoculation loop and grown overnight at 30° C. and 160 spm. The thus-obtained preculture fluid had an optical density (OD600) of 6.4 at a wavelength of 600 nm. As a medium for culture, a culture fluid was prepared by mixing yeast extract, sodium glutamate, glucose, lactose, inorganic salt and antifoaming agent in 2500 ml of distilled water. The prepared culture fluid was introduced into a 5-L culture tank (MDN-type 5L(S) available from B.E. MARUBISHI CO., LTD.) and subjected to steam sterilization for 30 minutes at 121° C. In the culture tank, 5 ml of the preculture fluid was axenically inoculated and grown while stirring for 40 hours at a temperature of 30° C. and a ventilation rate of 0.5 vvm. As a result, there was obtained the culture fluid in suspension form having an optical density (OD600) of 22. During the culture, the pH of the culture fluid was adjusted to about 7.0 with the use of a 20% aqueous sodium carbonate solution and a 42.5% aqueous phosphoric acid solution. After the culture, the ventilation rate was changed to 0 vvm. Then, 3-chloro-1,1-difluoro-2-propanone hydrate was added in an amount of 6.25% wt/v (156.25 g), that is, 90% wt/wt relative to the culture fluid. In this culture fluid, the hydrate was subjected to reduction reaction for 24 hours at a pH of 6.0 while the coenzyme was regenerated by glucose dehydrogenase. After the reaction, the rate of conversion to the target product compound was 99%; and the optical purity of the target product compound was 89.2% ee(S). The culture fluid after the reaction was subjected to vacuum distillation (inside pressure: 19.2 kPa, vapor temperature: 57 to 61° C.), thereby obtaining 526 g of an aqueous solution containing 85 g of (S)-1-chloro-3,3-difluoroisopropyl alcohol. The NMR data of the product compound was as follows: $^1$H-NMR (deuterated solvent: deuterated chloroform, reference material: tetramethylsilane) δ ppm: 3.72 (m, 2H), 4.03 (m, 1H), 5.86 (td, 1H); $^{19}$F-NMR (deuterated solvent: deuterated chloroform, reference material: hexafluorobenzene set as −162.2 ppm) −132.2 (ddd, 1F), −130.6 (ddd, 1F).

Reference Example 10

First, 1.0 equivalent of a 48% aqueous sodium hydroxide solution was dropped into 85 g of the aqueous (S)-1-chloro-3,3-difluoroisopropyl alcohol solution obtained in Reference Example 9 under cooling by ice water. The dropping was performed while monitoring and maintaining the temperature of the solution at 0 to 3° C. After the dropping, the resulting solution was subjected to ring-closing reaction by stirring for 120 minutes at 1° C. The solution was then subjected to distillation at a vapor temperature of 50 to 70° C. (atmospheric pressure), thereby obtaining 49 g of (R)-2-difluoromethylethylene oxide. The optical purity of this product compound was 89.1% ee as measured under the same analysis conditions as those of Reference Example 6. The NMR data of the product compound was as follows: $^1$H-NMR (deuterated solvent: deuterated chloroform, reference material: tetramethylsilane) δ ppm: 2.8-2.9 (m, 2H), 3.27 (m, 1H), 5.56 (td, 1H); $^{19}$F-NMR (deuterated solvent: deuterated chloroform, reference material: hexafluorobenzene set as −162.2 ppm) −125.2 (ddd, 1F), −122.5 (ddd, 1F).

Reference Example 11

To an aqueous solution containing 49 g of the (R)-2-difluoromethylethylene oxide obtained in Reference Example 10, 0.2 equivalents of a 20% aqueous sulfuric acid solution was added. The resulting solution was reacted by stirring for 7 hours at 60° C. After the reaction, the pH of the solution was adjusted to 5 with the addition of sodium hydroxide. An inorganic salt was filtered out from the solution. The solution was then subjected to vacuum distillation (inside pressure: 1.5 kPa, vapor temperature: 80 to 81° C.), thereby obtaining 46 g of (R)-3,3-difluoro-1,2-propanediol. The optical purity of this product compound was 89.2% ee as measured under the same analysis conditions as those of Reference Example 8. The NMR data of the product compound was as follows: $^1$H-NMR (deuterated solvent: deuterated acetonitrile, reference material: tetramethylsilane) δ ppm: 3.61 (m, 2H), 3.72 (m, 1H), 5.79 (td, 1H); $^{19}$F-NMR (deuterated solvent: deuterated acetonitrile, reference material: hexafluorobenzene set as −162.2 ppm) −130.9 (ddd, 1F), −128.2 (ddd, 1F).

Reference Example 12

First, isopropyl ether (78 ml) was added to 5.66 g (17.2 mmol) of the compound of the following formula obtained in Example 19. The resulting mixture was stirred at room temperature, followed by adding thereto a 1 M aqueous phosphoric acid solution (43 ml).

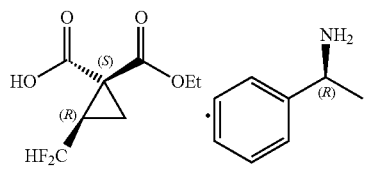

The mixture was further stirred for 30 minutes. Then, the mixture was left still for 20 minutes and thereby separated into two layers. The aqueous layer was removed. The organic layer was mixed with water (50 ml), stirred for 30 minutes and left still for 20 minutes. The organic layer was recovered and concentrated by a rotary evaporator. As a result, a compound of the following formula was obtained in an amount of 3.29 g (15.8 mmol).

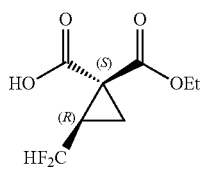

To 3.29 g (15.8 mmol) of this compound, toluene (32 ml), trimethylamine (3.20 g, 31.6 mmol) and t-butanol (3.51 g, 47.4 mmol) were added at room temperature. The resulting solution was heated to 70° C. Then, diphenylphosphoryl azide (6.52 g, 23.7 mmol) was gradually dropped into the solution. After the dropping, the solution was reacted for 15 hours while the temperature of the solution was set to 80° C. After the reaction, the solution was subjected to solvent evaporation by a rotary evaporator. The concentration residue was mixed by stirring with isopropyl ether (50 ml) and water. The resulting mixture was separated into two layers. The organic layer was recovered and similarly subjected to two-layer separation by mixing and stirring with water (35 ml). The organic layer was recovered and concentrated by a rotary evaporator, thereby yielding a crude product. A solution of potassium hydroxide (1.14 g, 20.4 mmol) in methanol (10 ml) was added to the crude product at room temperature. The resulting solution was subjected to hydrolysis reaction for 5 hours at 40° C. This reaction solution was cooled by ice water. Then, a 1 M aqueous phosphoric acid solution (20 ml) was gradually added to the reaction solution. Further, diisopropyl ether (50 ml) was added to the solution. The solution was stirred for 30 minutes at room temperature and separated into two layers. The organic layer was mixed with water (20 ml). The mixture was stirred for 30 minutes at room temperature and then separated into two layers. The thus-extracted organic layer was recovered and concentrated by a rotary evaporator. As a result, a compound of the following formula was obtained in an amount of 2.37 g (9.4 mmol).

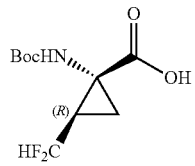

In the above formula, Boc represents a tert-butoxycarbonyl group.

Comparative Example 1

Into a 100-ml three-neck flask with a thermometer well, a three-way stopcock and a dropping funnel, dichloromethane (14 ml), 3,3-difluoro-1,2-propanediol of the following formula (water content: 0.47%, 1.0 g, 8.9 mmol) and imidazole (1.5 g, 22.3 mmol) were put. The contents of the flask were stirred for 20 minutes at room temperature.

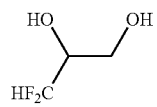

The thus-obtained reaction solution was cooled by of a dry ice-acetonitrile mixture (−45° C.). Then, a mixture of sulfuryl chloride (1.2 g, 8.9 mmol) and dichloromethane (3 ml) was added to the reaction solution through the dropping funnel over 2 hours and 30 minutes. At this time, the temperature of the reaction solution was −38 to −34.7° C. After the completion of the dropping, the reaction solution was stirred for 2 hours while the inside temperature of the flask was set to about −35° C. The reaction solution was further stirred overnight at room temperature. The reaction solution was analyzed by $^{19}$F-NMR. It was confirmed that: the reaction product was a complicated mixture; and the target compound of the following formula was not formed.

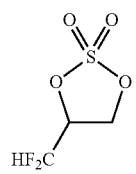

Comparative Example 2

Into a 20-ml two-neck flask with a thermometer well and a cock, difluoropropene oxide of the following formula (as a racemic mixture, purity: 44%, 8.9 g, 42.2 mmol) was put. The flask was cooled by ice water to an inside temperature of about 1° C.

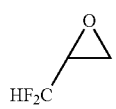

Next, a 48% aqueous solution of hydrobromic acid (7.47 g, 44.3 mmol) was gradually dropped into the flask. At this time, the inside temperature of the flask was 0 to 10° C.

After the completion of the dropping, the inside temperature of the flask was gradually raised to room temperature. The contents of the flask were stirred overnight. The thus-obtained reaction solution was subjected to extraction with the addition of methyl tert-butyl ether (15 ml). The resulting mixture was separated into two layers. The organic layer was concentrated by a flash distillation unit. As the concentration residue, a crude product of the target bromohydrin compound of the following formula was obtained in an amount of 9.2 g.

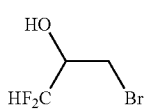

The content of the target compound in the crude product was 80 wt %. The yield of the target compound was almost quantitative. The NMR data of the target compound was as follows: $^1$H-NMR (deuterated solvent: deuterated acetonitrile, reference material: tetramethylsilane) δ ppm: 3.05 (m, 2H), 3.60 (m, 1H), 5.76 (td, 1H); $^{19}$F-NMR (deuterated solvent: deuterated acetonitrile, reference material: hexafluorobenzene set as −162.2 ppm) −130.3 (ddd, 1F), −127.6 (ddd, 1F).

Comparative Example 3

Into a 50-ml eggplant flask, the bromohydrin compound of the following formula (purity: 80 wt %, 4.3 g, 20 mmol) obtained in Comparative Example 2, paratoluenesulfonyl chloride (5.7 g, 30 mmol) and methyl tert-butyl ether (20 ml) were put. The flask was cooled by ice water.

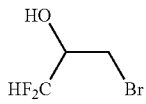

Next, triethylamine (3.0 g, 30 mmol) was gradually added into the flask. The contents of the flask were stirred for 30 minutes. The inside temperature of the flask was gradually raised to room temperature. The contents of the flask were stirred overnight. The thus-obtained reaction solution was washed four times with 20 ml of water. The solvent was removed from the reaction solution by a rotary evaporator. This solution was dehydrated by azeotropic dehydration with the addition of toluene, and then, further dehydrated with sodium sulfate. The resulting solid matter was filtered out. Finally, toluene was removed from the solid matter by a rotary evaporator. As a result, a crude product of the target compound of the following formula was obtained in an amount of 12.8 g. The content of the target compound was 34.9 mmol. The yield of the target compound was 87%.

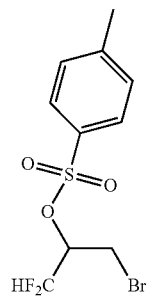

The NMR data of the target compound was as follows: $^1$H-NMR (deuterated solvent: deuterated chloroform, reference material: tetramethylsilane) δ ppm: 2.47 (s, 3H), 3.56 (m, 2H), 4.73 (m, 1H), 6.00 (dt, 1H), 7.37 (d, 2H), 7.83 (d, 2H); $^{19}$F-NMR (deuterated solvent: deuterated chloroform, reference material: hexafluorobenzene set as −162.2 ppm) −132.4 (ddd, 1F), −130.1 (ddd, 1F).

Comparative Example 4

In a 50-ml three-neck flask with a thermometer well, a septum and a three-way stopcock, sodium hydride (0.2 g, 5 mmol) was put. The inside of the flask was replaced by nitrogen. Next, DMF (20 ml) was put into the flask. The flask was cooled by ice water to an inside temperature of about 2° C. Diethyl malonate (0.8 g, 5 mmol) was gradually added into the flask. At this time, the inside temperature of the flask was 2 to 4° C. Subsequently, 1.8 g (5 mmol) of the crude product of the compound of the following formula obtained in Comparative Example 3 was gradually dropped into the flask.

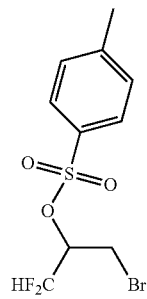

After the completion of the dropping, the thus-obtained reaction solution was gradually returned to room temperature and stirred overnight. The reaction solution was then analyzed. It was confirmed that the target malonate adduct of the following formula was not formed.

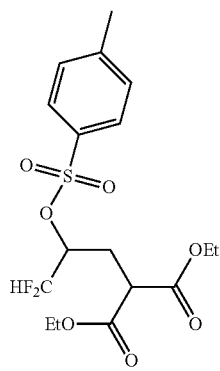

Comparative Example 5

Into a 30-ml two-neck flask with a thermometer well and a cock, chlorohydrin of the following formula (as a racemic mixture, purity: 75 wt %, 3.5 g, 20 mmol), methyl tert-butyl ether (20 ml) and paratoluenesulfonyl chloride (4.2 g, 22 mmol) were put. The flask was cooled by ice water to an inside temperature of about 2° C.

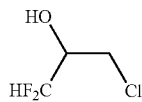

Next, trimethylamine (2.4 g, 24 mmol) was gradually dropped into the flask. At this time, the inside temperature of the flask was 2 to 3° C. After the completion of the dropping, the inside temperature of the flask was gradually raised to room temperature. The contents of the flask were stirred overnight at room temperature. The thus-obtained reaction solution was washed four times with 20 ml of water and separated into two layers. The organic layer was concentrated with the removal of the organic solvent by a rotary evaporator. The concentrated solution was dehydrated by azeotropic dehydration with the addition of toluene. The dehydrated solution was subjected to filtration and concentrated by a rotary evaporator. As a result, the target compound of the following formula was obtained in an amount of 4.6 g. The content of the target compound was 15 mmol. The yield of the target compound was 75%.

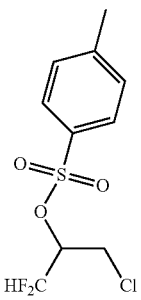

The NMR data of the target compound was as follows: $^1$H-NMR (deuterated solvent: deuterated chloroform, reference material: tetramethylsilane) δ ppm: 2.45 (s, 3H), 3.75 (m, 2H), 4.73 (m, 1H), 5.99 (dt, 1H), 7.36 (d, 2H), 7.82 (d, 2H); $^{19}$F-NMR (deuterated solvent: deuterated chloroform, reference material: hexafluorobenzene set as −162.2 ppm) −132.3 (ddd, 1F), −130.1 (ddd, 1F).

Comparative Example 6

In a 50-ml three-neck flask with a thermometer well, a septum and a three-way stopcock, sodium hydride (0.2 g, 5 mmol) was put. The inside of the flask was replaced by nitrogen. Next, DMF (20 ml) was put into the flask. The flask was cooled by ice water to an inside temperature of about 2° C. Diethyl malonate (0.83 g, 5.2 mmol) was gradually dropped into the flask. At this time, the inside temperature of the flask was 2 to 7° C. Subsequently, the compound of the following formula (1.4 g, 5 mmol) obtained in Comparative Example 5 was gradually dropped into the flask.

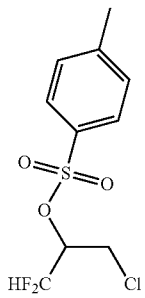

After the completion of the dropping, the thus-obtained reaction solution was gradually returned to room temperature and stirred overnight. The reaction solution was then analyzed. It was confirmed that the target malonate adduct of the following formula was not formed.

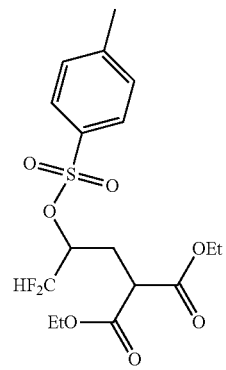

Comparative Example 7

Into a 100-ml three-neck flask with a thermometer well, a Dimroth condenser and a cock, the 3,3-difluoro-1,2-propanediol of the following formula (purity: 83.7 wt %, 5.0 g, 38 mmol) obtained in Reference Example 2, methyl tert-butyl ether (38 ml) and paratoluenesulfonyl chloride (21.7 g, 114 mmol) were put. The flask was cooled by ice water to an inside temperature of about 2° C.

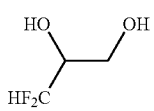

Next, trimethylamine (15.4 g, 152 mmol) was gradually dropped into the flask. After the completion of the dropping, the flask was heated in an oil bath to an inside temperature of about 47° C. and kept heated at this temperature for 2 hours. After that, the contents of the flask were stirred overnight at room temperature. The thus-obtained reaction solution was mixed with 20 ml of water and separated into two layers. The organic layer was again subjected to two-layer separation with the addition of 10 ml of water and 10 ml of methyl tert-butyl ether. Further, the organic layer was washed with 10 ml of water and twice with 5 ml of a saturated aqueous sodium chloride solution and separated into two layers. This organic layer was subjected to solvent evaporation by a rotary evaporator and concentrated by azeotropic dehydration with the addition of toluene. As paratoluenesulfonic acid remained in the concentration residue, the concentration residue was subjected to two-layer separation by adding 50 ml of methyl tert-butyl ether and 30 ml of toluene to the concentration residue and washing the resulting mixture with a mixed liquid of 10 ml of water and 3.2 g (38 mmol) of sodium hydrogencarbohate and then with 10 ml of water. The thus-obtained organic layer was subjected to solvent evaporation by a rotary evaporator. As a result, a crude product of the target compound of the following formula was obtained in an amount of 16.9 g.

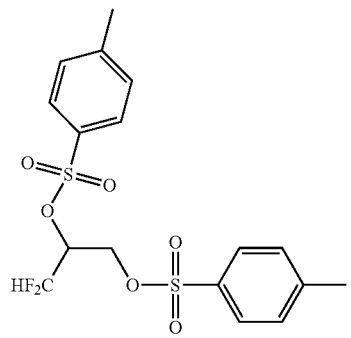

By $^{19}$F-NMR analysis of the crude product, it was confirmed that: the content of the target compound was 38 mol; and the reaction proceeded almost quantitatively. Then, 3 g of the crude product was purified by column chromatography. There was resultantly obtained 2.56 g of the purified target compound. The NMR data of the target compound was as follows: $^1$H-NMR (deuterated solvent: deuterated chloroform, reference material: tetramethylsilane) δ ppm: 2.47 (s, 6H), 4.17 (ddd, 1H), 4.26 (ddd, 1H), 4.69 (m, 1H), 5.90 (dt, 1H), 7.36 (d, 4H), 7.71 (d, 2H), 7.77 (d, 2H); $^{19}$F-NMR (deuterated solvent: deuterated chloroform, reference material: hexafluorobenzene set as −162.2 ppm) −132.2 (ddd, 1F), −128.7 (ddd, 1F).

Comparative Example 8

Into a 50-ml three-neck flask with a thermometer well, a Dimroth condenser and a cock, sodium hydride (0.2 g, 5 mmol) was put. After the inside of the flask was replaced by nitrogen, DMF (20 ml) was put into the flask. The flask was cooled by ice water to an inside temperature of about 3° C. Next, diethyl malonate (0.8 g, 5 mmol) was gradually dropped into the flask. At this time, the inside temperature of the flask was 3 to 4° C. Subsequently, a mixture of the purified compound of the following formula (2.56 g, 6 mmol) obtained in Comparative Example 7 and 5 ml of DMF were gradually dropped into the flask.

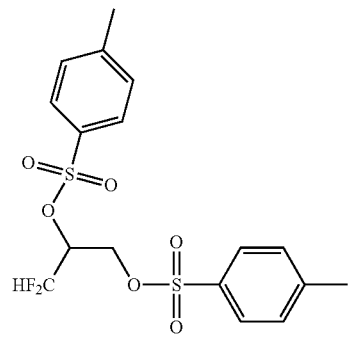

At this time, the inside temperature of the flask was 3 to 5° C. While the flask was cooled by ice water, the contents of the flask were stirred for 30 minutes. The flask was heated in an oil bath to an inside temperature of 50° C. The contents of the flask was then stirred for 4 hours at this temperature. The contents of the flask were further stirred overnight at room temperature. The thus-obtained reaction solution was analyzed. It was confirmed that the target malonate adduct of the following formula was not formed.

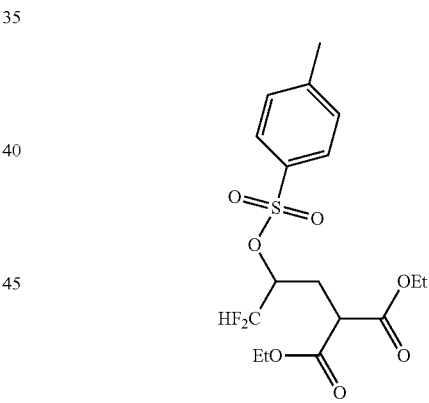

Comparative Example 9

Into a 100-ml three-neck flask with a thermometer well, a cock and a Dimroth condenser, DBU (2.62 g, 17.2 mmol) and THF (29.7 ml) were put. The flask was cooled by ice water. Next, diethyl malonate (2.76 g, 17.2 ml) was dropped into the flask. While the flask was kept cooled by ice water, the contents of the flask were stirred for 30 minutes. The inside temperature of the flask was raised to room temperature. Subsequently, a mixture of a fluorine-containing cyclic sulfate of the following formula (as a racemic mixture, 3.0 g, 17.2 mmol), 5.7 ml of THF and benzotrifluoride (1.46 g, 10 mmol) as an internal standard material was gradually dropped into the flask.

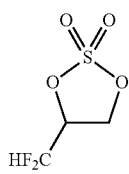

At this time, the inside temperature of the flask was 22 to 37° C. The contents of the flask were stirred for 2 hours at room temperature. To the thus-obtained reaction solution, DBU (3.14 g, 20.7 mmol) was added. The reaction solution was heated for 1 hour and 45 minutes by an oil bath at about 65° C. After that, the reaction solution was cooled to room temperature and then analyzed by NMR. The target cyclopropane compound of the following formula was not confirmed by the analysis.

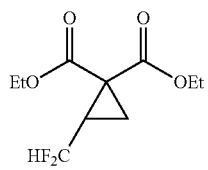

Comparative Example 10

Into a 100-ml three-neck flask with a thermometer well, a three-way stop cock and a dropping funnel, THF (19 ml), 3,3-difluoro-1,2-propanediol of the following formula (water content: 0.47%, 5.6 g, 50 mmol) and trimethylamine (13.7 g, 135 mmol) were put. The contents of the flask were stirred for 20 minutes at room temperature.

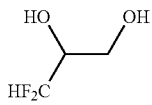

The thus-obtained reaction solution was cooled to 0° C. by a coolant of −5° C. Subsequently, a mixture of sulfuryl chloride (8.1 g, 20 mmol) and dichloromethane (11 ml) was dropped into the reaction mixture over 15 minutes while the temperature of the reaction solution was maintained at 0° C. After the completion of the dropping, the temperature of the reaction solution was raised to 20° C. When the reaction solution was stirred for 1 hour at this temperature, the rate of conversion of the reactant became 100%. The reaction solution was analyzed by $^{19}$F-NMR. It was confirmed that: the reaction product was a complicated mixture; and the target compound of the following formula was not contained in the reaction product.

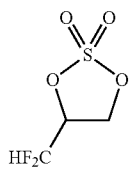

INDUSTRIAL APPLICABILITY

The fluorine-containing cyclopropane carboxylic acid compound, which is the target compounds of the present invention, is useful as an intermediate for pharmaceutical and agrichemical products.

The invention claimed is:

1. A method of producing a fluorine-containing cyclic sulfate of the general formula [2], comprising: reacting a fluorine-containing diol compound of the general formula [1] with sulfuryl fluoride in the presence of at least one basic compound selected from the group consisting of alkali metal hydrides, alkaline earth metal hydrides, alkali metal hydroxides, alkaline earth metal hydroxides, alkali metal carbonates, alkaline earth metal carbonates, alkali metal hydrogencarbonates and alkaline earth metal hydrogencarbonates

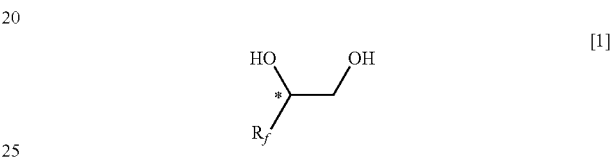

where $R_f$ represents a $C_1$-$C_6$ linear or branched fluoroalkyl group having at least one fluorine atom; and * represents an asymmetric carbon atom

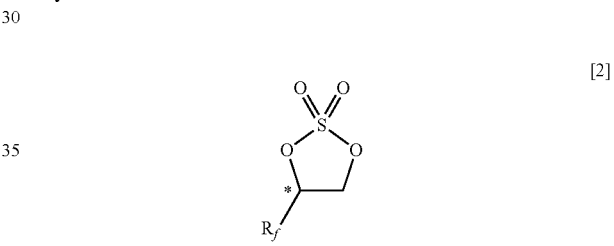

where $R_f$ represents the same group as defined in the general formula [1]; and * represents an asymmetric carbon atom.

2. The method according to claim 1, wherein $R_f$ is a difluoromethyl group or a trifluoromethyl group.

3. The method according to claim 1, wherein the fluorine-containing diol compound is reacted with the sulfuryl fluoride in a temperature range of −50 to +50° C.

4. The method according to claim 1, wherein the sulfuryl fluoride is used in an amount of 0.7 to 4.0 equivalents.

5. A method of producing a fluorine-containing cyclopropane diester of the general formula [5] comprising: producing the fluorine-containing cyclic sulfate by the method according to claim 1; and reacting the fluorine-containing cyclic sulfate with a malonic diester of the general formula [3] in the presence of an inorganic base

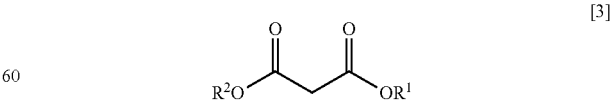

where $R^1$ and $R^2$ each independently represents a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group

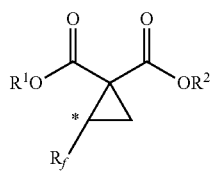

[5]

where $R_f$ represents the same group as defined in the general formula [1] of claim 1; $R^1$ and $R^2$ represents the same groups as defined in the general formula [3]; and * represents an asymmetric carbon atom.

6. The method according to claim 5, wherein the inorganic base is an alkali metal, an alkali metal hydride, an alkaline earth metal hydride, an alkali metal hydroxide or an alkaline earth metal hydroxide.

7. The method according to claim 5, wherein the fluorine-containing cyclic sulfate of the general formula [2] and the malonic diester of the general formula [3] are added into a solvent containing the inorganic base.

8. A method of producing a fluorine-containing cyclopropane monoester of the general formula [7], comprising: producing the fluorine-containing cyclopropane diester by the method according to claim 5; and performing hydrolysis of the fluorine-containing cyclopropane diester in the presence of an alkali metal hydroxide, an alkaline earth metal hydroxide, an alkali metal carbonate, an alkaline earth metal carbonate, an alkali metal hydrogencarbonate, an alkaline earth metal hydrogencarbonate or a quaternary ammonium hydroxide of the general formula [6]

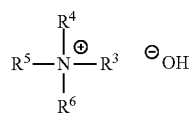

[6]

where $R^3$, $R^4$, $R^5$ and $R^6$ each independently represents a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group; and two or more of $R^3$, $R^4$, $R^5$ and $R^6$ may form a part of the same aliphatic ring or aliphatic aromatic ring

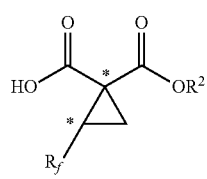

[7]

where $R_f$ represents the same group as defined in the general formula [1] of claim 1; $R^2$ represents the same group as defined in the general formula [3] of claim 5; and * represents an asymmetric carbon atom.

9. The method according to claim 8, wherein the hydrolysis is performed at a temperature of −30 to +40° C.

10. The method according to claim 8, further comprising: adding an amine of the general formula [8] to the fluorine-containing cyclopropane monoester, thereby forming a salt of the fluorine-containing cyclopropane monoester and the amine as represented by the general formula [9]; and purifying the salt by recrystallization

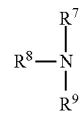

[8]

where $R^7$, $R^8$ and $R^9$ each independently represent a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group

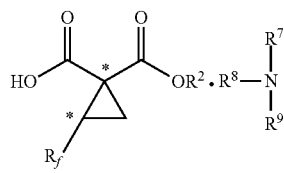

[9]

where $R_f$ represents the same group as defined in the general formula [1]; $R^2$ represents the same group as defined in the general formula [3] of claim 5; and $R^7$, $R^8$ and $R^9$ represent the same groups as defined in the general formula [8].

11. The method according to claim 10, wherein the amine of the general formula [8] is an amine of the general formula [10]:

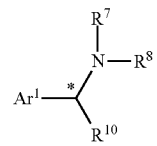

[10]

where $R^7$, $R^8$ and $R^{10}$ each independently represent a hydrogen atom, a $C_1$-$C_{18}$ alkyl group or substituted alkyl group having a linear or branched structure or a cyclic structure (in the case of three or more carbon atoms), or a $C_6$-$C_{18}$ aromatic ring group or substituted aromatic ring group; $Ar^1$ represents a $C_6$-$C_{14}$ aromatic ring group or substituted aromatic ring group; and, when $R^{10}$ is a $C_1$-$C_{18}$ alkyl group or substituted alkyl group having a linear or branched structure or a cyclic structure (in the case of three or more carbon atoms) or a $C_6$-$C_{18}$ aromatic ring group or substituted aromatic ring group, * represents an asymmetric carbon atom.

12. A salt of fluorine-containing cyclopropane monoester and amine as represented by the formula [17]

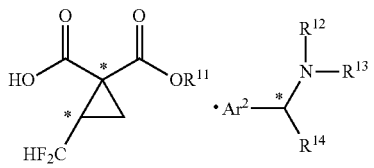

[17]

where $R^{11}$ represents a $C_1$-$C_6$ linear or branched alkyl group; $R^{12}$, $R^{13}$ and $R^{14}$ each independently represent a hydrogen atom, or a $C_1$-$C_6$ linear or branched alkyl group; $Ar^2$ represents a $C_6$-$C_{10}$ aromatic ring group or substituted aromatic ring group; and, when $R^{14}$ is a $C_1$-$C_6$ linear or branched alkyl group, * represents an asymmetric carbon atom.

* * * * *